(12) United States Patent
Boyd et al.

(10) Patent No.: US 8,133,241 B2
(45) Date of Patent: Mar. 13, 2012

(54) ARTICULATED ELEMENTS AND METHODS FOR USE

(75) Inventors: Robert R. Boyd, Jacksonville, FL (US); B. Matt Bartilson, Hilliard, OH (US); William T. Hanna, Gahanna, OH (US); Lynn Faulkner, Westerville, OH (US); Thomas D. Haubert, Columbus, OH (US); C. Michael Gegenheimer, Columbus, OH (US); Holly A. Stein, Columbus, OH (US); Jean E. Schelhorn, Granville, OH (US); James B. Gleeson, Columbus, OH (US); Mary Hoffman Pancake, Gahanna, OH (US); Brian C. Kelley, Pataskala, OH (US); Roger W. Smith, Grove City, OH (US); Kevin M. Taylor, Upper Arlington, OH (US); Dov S. Rosenberg, Cincinnati, OH (US); Wayne L. Poll, New Albany, OH (US)

(73) Assignee: Battelle Memorial Institute, Columbus, OH (US)

( * ) Notice: Subject to any disclaimer, the term of this patent is extended or adjusted under 35 U.S.C. 154(b) by 1106 days.

(21) Appl. No.: 10/538,459

(22) PCT Filed: Dec. 10, 2003

(86) PCT No.: PCT/US03/39511
§ 371 (c)(1),
(2), (4) Date: Dec. 12, 2007

(87) PCT Pub. No.: WO2004/052594
PCT Pub. Date: Jun. 24, 2004

(65) Prior Publication Data
US 2008/0086854 A1    Apr. 17, 2008

Related U.S. Application Data

(60) Provisional application No. 60/432,558, filed on Dec. 10, 2002, provisional application No. 60/432,563, filed on Dec. 10, 2002.

(51) Int. Cl.
*A61B 17/08* (2006.01)
(52) U.S. Cl. ....................................................... 606/151
(58) Field of Classification Search .......... 606/139–143, 606/151–158, 213–216, 219, 220, 224, 228–233; 623/23.72
See application file for complete search history.

(56) References Cited

U.S. PATENT DOCUMENTS
2,024,982 A    12/1935   Scott
(Continued)

OTHER PUBLICATIONS

Ziyan M. Hijazi, MD, (Professor and Chief, Section of Pediatric Cardiology. The University of Chicago Children's Hospital, Chicago, Illinois), "How Amplatzer Devices Work (Comparison of ASD Occlusion Devices)," AGA Medical Corporation, Copyright 1997-1999, Web Address: How Antplatzor Devices Work: AGA M . . . Jan. 21, 2002 4:12:23 PM, AGA Medical Corporation.

*Primary Examiner* — Melanie Tyson
(74) *Attorney, Agent, or Firm* — Richard M. Klein; Fay Sharpe LLP

(57) ABSTRACT

The present invention relates to a one-step fastening device, a process for creating a fastener utilizing such a device, and the end fastener produced thereby. In this regard, the invention uses an outer, hollow fastener material that can be partially compressed under tension at designated areas (i.e., a compression member) and an inner activation or tensioning member. The compression of the outer fastener material occurs at one or more flexible areas or compression features specifically located on the longitudinal axis of the material. As a result, the outer compression member is capable of being distorted or bent under tension to produce a predetermined configuration. The device described herein has the ability to form specific and controllable fasteners of designated shapes and configurations. Methods for fastening, snaring, gripping, cutting, and manipulating material using the device in a confined space are also provided.

33 Claims, 17 Drawing Sheets

U.S. PATENT DOCUMENTS

| | | |
|---|---|---|
| 2,820,269 A | 1/1958 | Wolfe |
| 4,577,631 A | 3/1986 | Kreamer |
| 4,589,410 A | 5/1986 | Miller |
| 4,694,541 A | 9/1987 | Skyba |
| 4,754,531 A | 7/1988 | Skyba |
| 4,860,408 A | 8/1989 | Johnson |
| 4,993,128 A | 2/1991 | Gold |
| 5,259,377 A | 11/1993 | Schroeder |
| 5,404,057 A | 4/1995 | Hasegawa |
| 5,807,405 A | 9/1998 | Vanney |
| 5,816,458 A | 10/1998 | Yonenoi |
| 5,893,880 A | 4/1999 | Egan et al. |
| 5,941,901 A | 8/1999 | Egan |
| 5,964,765 A | 10/1999 | Fenton, Jr. et al. |
| 6,106,545 A | 8/2000 | Egan |
| 6,174,324 B1 | 1/2001 | Egan et al. |
| 6,190,353 B1 | 2/2001 | Makower |
| 6,202,263 B1 | 3/2001 | Harker |
| 6,217,591 B1 | 4/2001 | Egan et al. |
| 6,231,587 B1 | 5/2001 | Makower |
| 6,286,746 B1 | 9/2001 | Egan et al. |
| 6,321,749 B1 | 11/2001 | Toti et al. |
| 6,358,271 B1 | 3/2002 | Egan et al. |
| 6,513,210 B1 | 2/2003 | Gonzalez |
| 6,530,934 B1 * | 3/2003 | Jacobsen et al. .............. 606/157 |
| 6,607,541 B1 * | 8/2003 | Gardiner et al. .............. 606/151 |
| 2003/0036748 A1 * | 2/2003 | Cooper et al. .................... 606/1 |

* cited by examiner

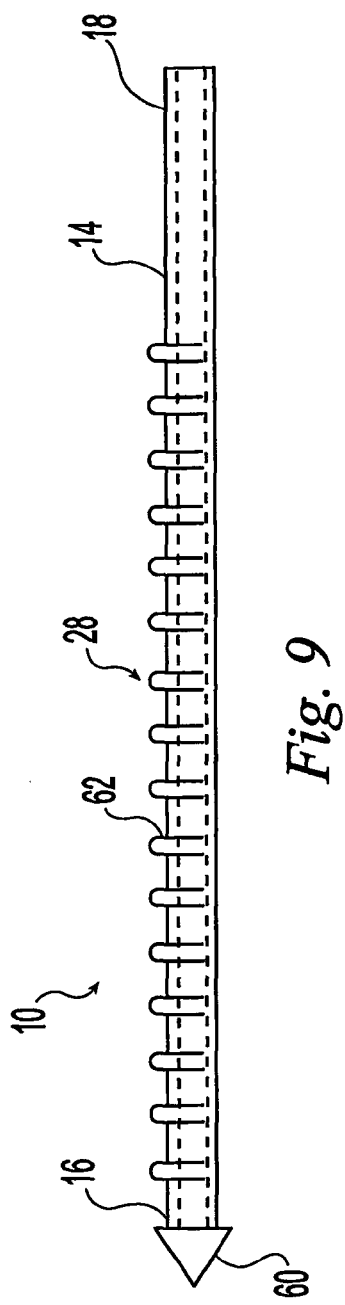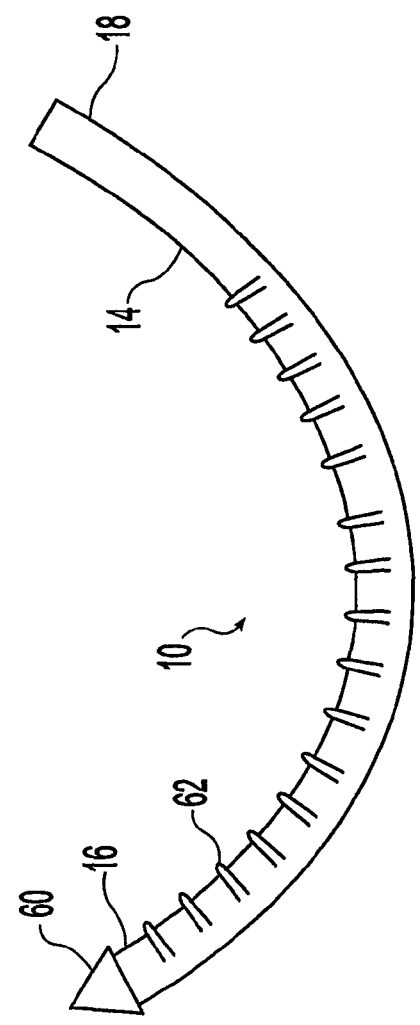

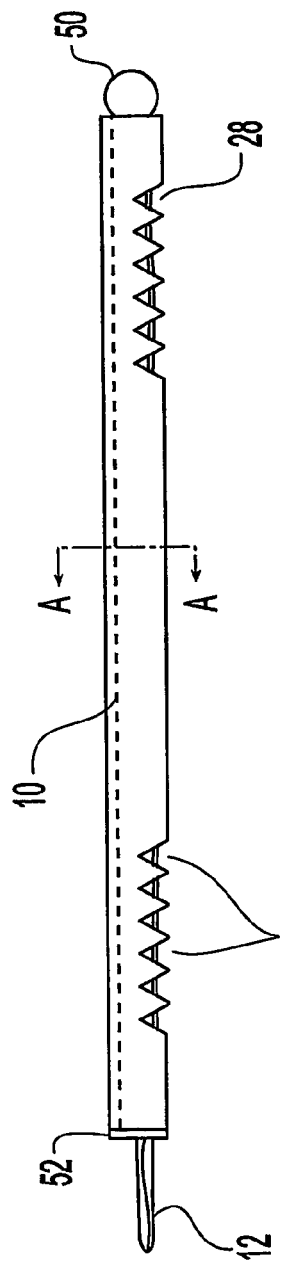
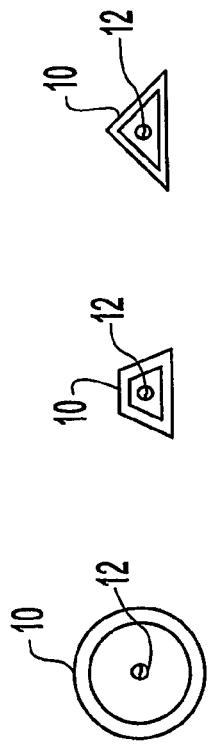
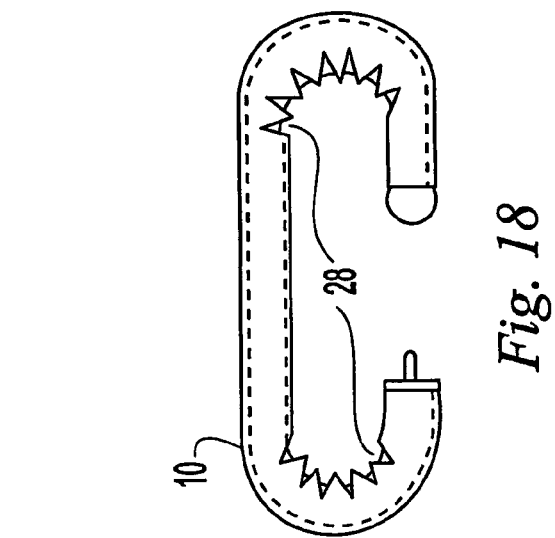
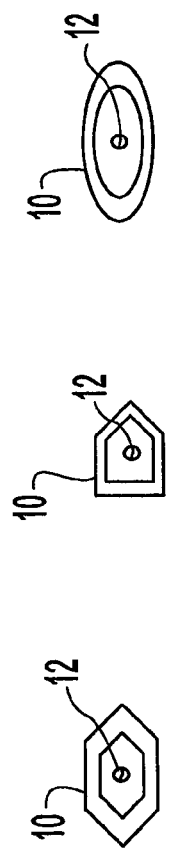

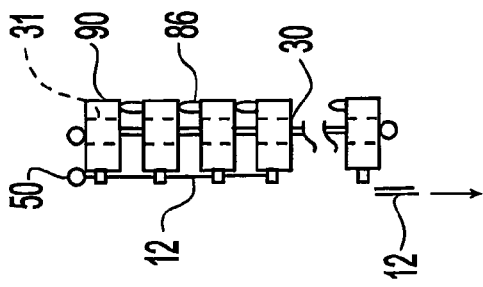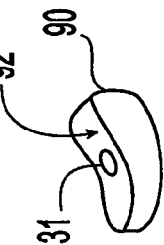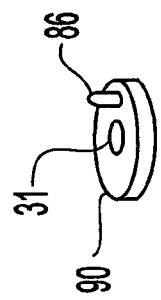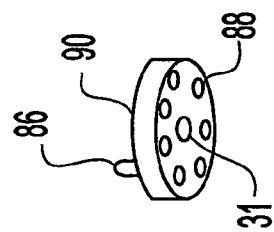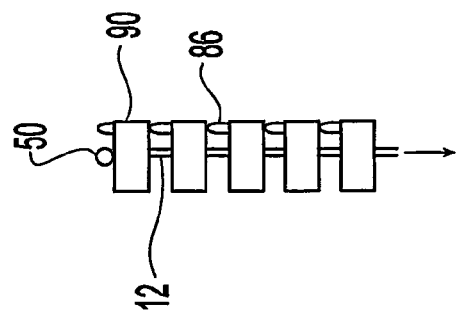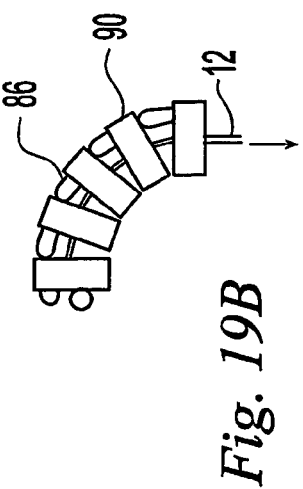

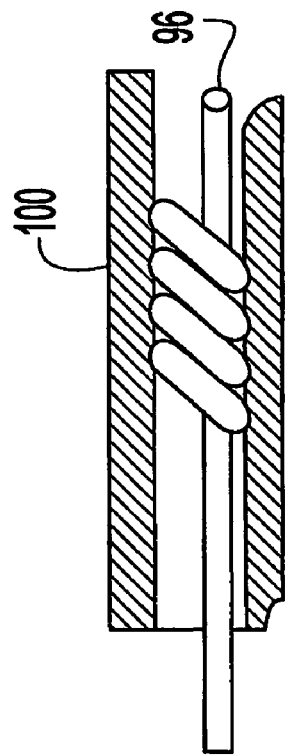
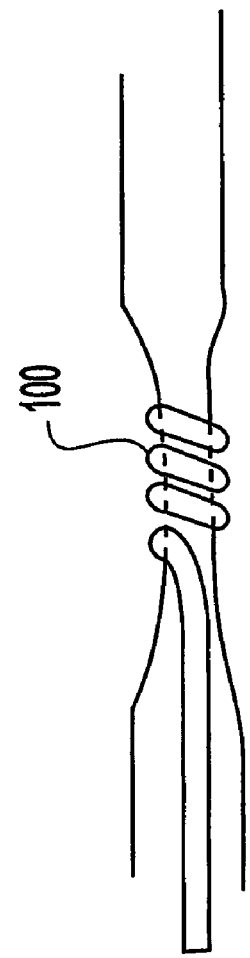
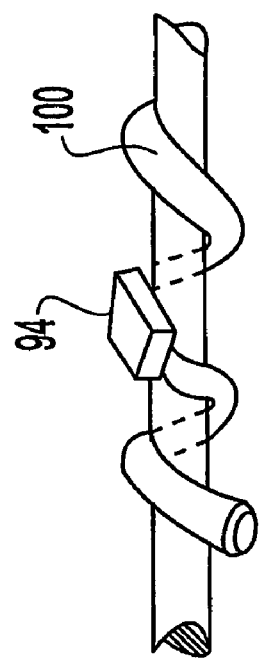
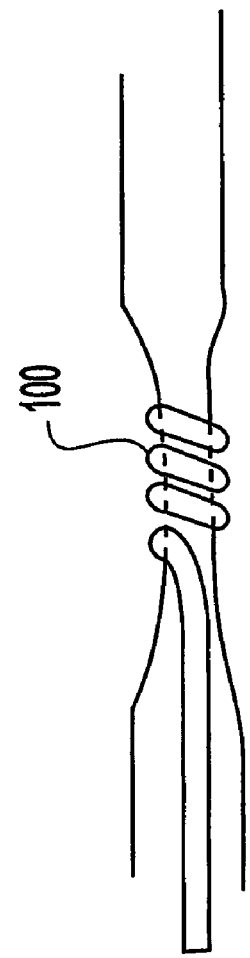

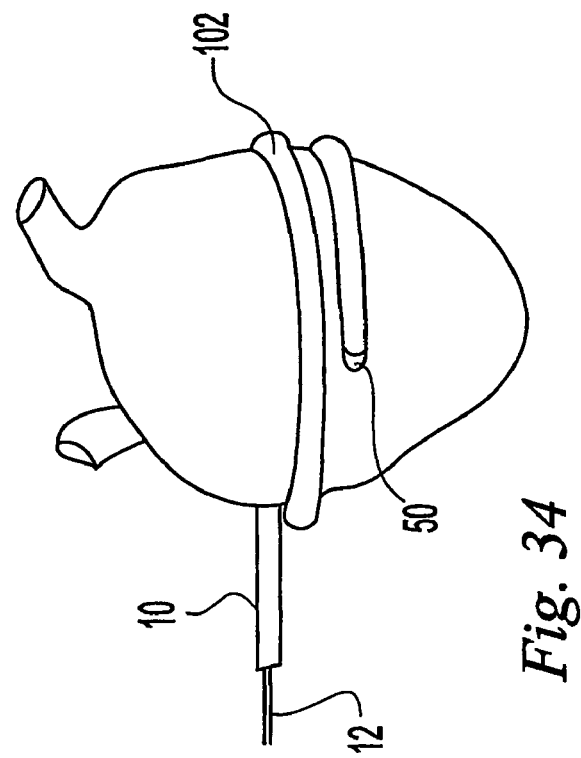
Fig. 34
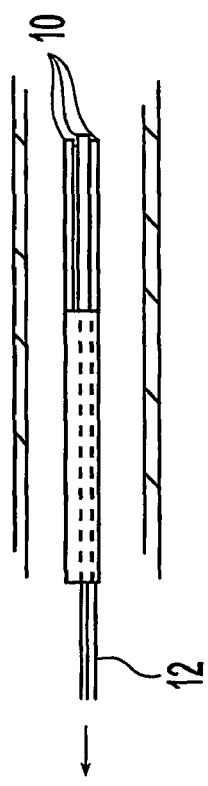
Fig. 32
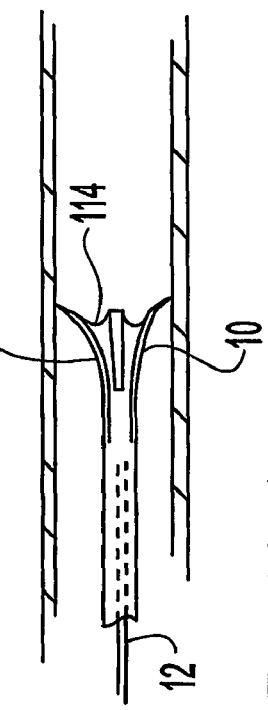
Fig. 33-A
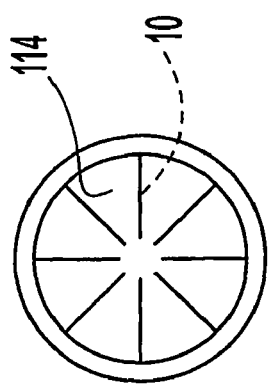
Fig. 33-B

ARTICULATED ELEMENTS AND METHODS FOR USE

CROSS REFERENCE TO RELATED APPLICATIONS

This application incorporates by reference and claims the benefit of U.S. provisional application Ser. No. 60/432,558, filed Dec. 10, 2002; and U.S. provisional application Ser. No. 60/432,563, filed Dec. 10, 2002.

FIELD OF THE INVENTION

The present invention relates generally to the art of fasteners and methods of fastening and, in particular, to a fastener apparatus having flexibility and wide range of uses. The invention finds particular application in any procedure where control of the insertion path of a fastener in a confined space are necessary, and can serve to fasten, capture, snare, cut, secure, grip, move, manipulate and perform other operations on materials or objects.

BACKGROUND OF THE INVENTION

Stapling is a means for fastening materials together. Staples are usually U-shaped lengths of wire that are pushed through material and bent over on an anvil. A variety of specific stapler devices exist which are application-specific (i.e., circular staplers, linear staplers, etc.).

Other devices are used for attachment, snaring or grasping an object to capture or move it, permanently or temporarily. This broad category of devices involves a variety of tools and techniques, and some applications require specialized tools to function in a limited space.

The need exists for fasteners, snares, cutting and gripping devices that may be deployed in a confined environment in a flexible manner that can be used with confidence. The present invention contemplates new and improved devices and methods for fastening, attaching, securing, snaring, cutting, moving, manipulating or gripping objects that overcome problems with other devices and methods for achieving such results.

SUMMARY OF THE INVENTION

The present invention meets the needs for improved flexibility and capability in devices used for fastening, snaring, cutting, attaching, moving manipulating, gripping and the like.

One preferred embodiment of the present invention relates to a one-step attachment device, a method for utilizing such a device, and the final fastener produced thereby. The device described herein has the ability to form specific and controllable fasteners of designated shapes and configurations.

More generally, this preferred embodiment of the present invention uses an outer, hollow fastener material that can be partially compressed at designated areas (i.e., a compression member) and an inner activation or tensioning member. The compression of the outer fastener material occurs at one or more flexible areas or compression features specifically located on the longitudinal axis of the material. As a result, the outer compression member is capable of being distorted or bent to produce a predetermined configuration.

Along these lines, the inner tensioning member is preferably movably positioned within the outer compression member. It is also operably connected with the outer compression member for selectively applying compression to the outer member by placing the inner tensioning member under tension. When tension is applied to the inner tensioning member, the portion of the outer compression member containing the flexible areas becomes deformed producing, for example, a curved shape or loop. The final configuration of the outer compression member is dependent upon the amount of tension applied by the inner tensioning member and the overall design of the flexible areas of the compression member.

In this regard, the flexible area(s) are preferably designed to be located on substantially one side of the longitudinal axis of the outer compression member, but may be placed on different sides of the outer compression member to make complex fastener shapes. Thus, dependent upon the number, size and shape, and location of the flexible areas, a wide variety of designs can be created upon activation or tensioning of the compression member.

Preferably, the compression member is tubular, i.e. circular in cross-section. However, other cross-sectional configurations, such as other geometric shapes or combinations of geometric shapes, may be used.

The present invention can be independently utilized to perform a task, or it can be used in conjunction with a deployment device to itself place or use another tool or instrument. Consequently, multiple techniques and methods of usage are possible for the present invention, and its uses are many.

The device of the present invention is useful in the process of attaching one portion of material, whether physical or biological, to another. Additionally, it is useful in other applications where it is necessary to form specific shapes and perform specific functions such as grasping, clamping, cutting and snaring.

The device of the present invention has the ability to form standard and unique shapes. Moreover, with the addition of a piercing tip, the device is capable of simultaneous penetration of a material and fastener coiling, as well as independent control of these actions. This makes it possible to insert and produce a complete fastener while operating motions are contained or limited to one plane of movement.

In another aspect, the present invention is directed to a fastening device comprising an outer, hollow, tubular type compression member and an inner tensioning member slidably movably received therein. The outer tubular compression member is designed in such a manner that when the inner tensioning member is activated (or tensioned), the compression member is at least partially compressed along at least a portion of one side of its longitudinal axis. For example, the outer tubular compression member can be configured to have various degrees of material thickness with one side (i.e., the rigid side) of the tube being thick-walled and the other side (i.e., the flexible side) being thin-walled at selective places. The inner tensioning member is operably connected with the compression member for selectively applying compression to the compression member. When the tensioning member is activated, the flexible, thin-walled or flexible side of the outer tube will at least partially collapse and the compression member will assume a curved shape. By adjusting the composition of the flexible, thin-walled side, various curved or loop-like configurations can be produced.

Similarly, the flexible side of the compression member can be notched, grooved, indented, cut or slit at one or more locations to the same or different depths, widths or angles. Upon activation by the inner tensioning member, the compression member will be at least partially compressed or bent in one or more designated locations. Alternatively, the flexible side of the compression member can be corrugated, and/or corrugated and slit, grooved, indented, etc., allowing for deformation to occur on that side.

Moreover, one or more areas of the flexible side of the preferred tubular compression member can also be structurally weakened, such as by chemical etching, abrasion blasting, etc. In such an aspect, the tubular compression member will preferentially bend in a predetermined manner to form the desired, non-linear fastener shape.

The compression member may also be made of sections having different sections connected serially. Such sections may be rotated and adjusted by the user to customize the shape and produce a desired configuration upon compression. Use of one or more tensioning members extending through or along the sections can make possible the application of compressive forces as desired on all or portions of the sections.

Thus, the compression member can be formed from a continuous material, or from a series of discontinuous sections, or combinations thereof. If formed of a contiguous material, uncut areas of the material, preferably tubular, can act as a backbone or as a series of hinges, allowing for deformation of the material at the "link" interfaces In a further aspect, the invention is directed to a one-shot (i.e. staple-like) attachment formed from a device comprising at least a hollow compression member and an inner tensioning member. The compression member is preferably tubular in configuration and is designed such that when it is compressed, it deforms and/or aligns along predetermined locations. The deformation and/or alignment are limited by the design and configuration of the material of the compression member and the amount of tension applied. Thus, for example, a u-shaped fastener with a rigid center portion and movable tips on the ends that start out perpendicular to the rigid center portion may be inserted and re-configured into the flattened "B" shape of a compressed standard staple by applying tension via the inner tensioning members to compress the compression members that form the movable tips.

In this regard, one side of the compression member is designed to be more flexible than the other side. In turn, the tensioning member is operably connected with the compression member for selectively applying compression to the compression member when the inner tensioning member is placed in tension. For example, the distal end of the tensioning member can be attached to the distal end of the compression member. The proximal end of the tensioning member can then be placed under tension resulting in deformation of one side of the compression member to form a curved surface or loop.

In this aspect of the invention, the compression member can be constructed in several ways. It can be made of a hollow linear member having flexible and rigid sides. Additionally, it can comprise divided interfacing or interconnecting links having predetermined areas of collapse or movement when under compression. The interconnected links of the compression member are designed such that when they are placed under compression and are pulled together by the tensioning member, they stack in a prescribed fashion to form a specific shape. Consequently, the compression member can be formed from a one-piece material having a rigid side and at least one flexible side, or by forming individual sections and separately stringing them together to form a rigid side and a flexible side, or a series of rigid and flexible segments along the compression member. The term links and sections may be used interchangeably in describing the invention, as both types of devices described immediately above are useful in practicing the applications described herein, although one may be more effective than another in a particular application. Groups of links or sections may also be referred to as segments herein.

In still another aspect, the present invention is directed to a device for fastening materials. The device comprises a hollow tubular compression member and a tensioning device. The compression member is designed in such a manner that when the tensioning member is activated or tensioned, the compression member deforms or compresses on one side of its linear axis so as to form a predescribed shape such as a circle, ellipsoid, etc.

In another further aspect, a fastening device is provided. The device comprises a preferably tubular member which can be compressed at one or more flexible areas located on one side of the tube to form a permanent or semi-permanent shape, such as a curve or loop, when a tensioning member is tensioned or pulled through or along side the compression member. Preferably, the compression member is formed of small gage stainless steel tubing and the tensioning member consists of a stainless steel line or cable. However, other types of materials include, but are not limited to, metals (such as titanium, Nitinol™ or other memory alloys, or any biocompatible metal or alloy), resorbable or non-resorbable polymers, natural materials, ceramics, or combinations thereof. One or more notches, slits or cutouts are present on one side or alternate sides of the preferably tubular compression member to produce the flexible areas, although alternatively such features can result from a compression member made of a series of sections as described above. The tensioning member is operably connected with the compression member in such a manner as to compress the flexible areas of the compression member upon application of tension The compression member may also be formed of material that fails to produce a permanent shape upon compression. In such an embodiment, the end of the tensioning member can be attached to the compression member in order to maintain the compression members shape or configuration. Alternatively, several approaches can also be utilized in order to maintain the pressure on the outer compression member subsequent to activation. These approaches include the activation of one-way cable-retention clamps, securement devices, or other apparatuses, welding, crimping and the like, as discussed further below.

The device of this aspect of the invention can be deployed manually, but also in combination with an insertion device such as a catheter. The device can be deployed while simultaneously or systematically tensioning the line or cable. Simultaneous and independent fastener insertion and curvature can be accomplished by independently controlling the extension of the fastener and the cable tension. When the device is curved and placed where desired, the end of the tensioning device can be fixed, such as attached to the compression member, and released from the outside tensioning provider.

In an alternative embodiment to this aspect, the deformation areas of the side wall(s) of the outer compression member can be adjusted to produce the curve, loop or overall configuration desired. In this regard, weaker or thinner sections will deform earlier than the stronger or thicker sections. This allows for a method of designing various shapes, formations and functionality into the compression member.

In another aspect, the device of the present invention preferably consists of an outer, hollow tubular compression member and an inner tensioning member. The tubular compression member comprises of a plurality of notches on one side or is made up of a plurality of tubular sections. The application of tension to the tensioning cable causes the tubular section to curl and thereby creating a loop. The end of the tensioning member is then attached, clamped, locked, welded, sealed, or crimped to the outer tubular member in order to sustain or maintain the tension.

Alternatively, a removable inner tensioning cable may be applied. In such an application, the inner tensioning member is designed to break free from the compression member of the fastener or clip under higher forces than are required to form the fastener. This application is particularly beneficial in circumstances wherein the mechanical strength of the post-tension fastener or clip is produced by the material (e.g., stainless steel, Nitinol™, other metals and materials, memory materials) of the compression member.

In another aspect, the present invention relates to a fastening device comprising two or more compression members that are initially linearly arranged (i.e. in series) and a tensioning member. The outer compression members are operably interconnected in such a manner to produce a non-linear fastener upon activation of the tensioning member. The individual compression members can be designed to produce certain non-linear configurations upon activation. Such a device allows for straight insertion and controlled curling upon activation. Additionally, several individual compression members can be utilized in order to produce multiple loops for one fastener. As with the other embodiments disclosed above, such a device can be manually used or deployed through (i.e. from the inside of) another deployment tool. By way of example and not limitation, deployment tools may include sleeves, tubes, hoses or catheters.

In a further aspect, the present invention concerns the use of a compression member and a tensioning member to produce a capturing or clamping device. The structure of the capturing or clamping device is similar to that of the fastening device wherein a loop or desired shape is formed at the point at which the object is to be grabbed or captured. This device offers an advantage over alternative capture, snaring or removal devices in that the loop can be introduced and removed in a straight format while taking the shape necessary to grasp the object once it is positioned near the object.

Another advantage of this aspect of the invention is its ability to curl around and compress against the object to be removed. Traditional snaring devices consist of loops that must be slid over the end of an object. They are impractical when the ends of the object are not reachable or are of a size and geometry that prevents a loop from sliding over an end.

In a similar aspect, the present invention is directed to the self-coiling snare or capturing device discussed above further incorporating materials and a system that enables the capturing device to be heated, cooled or otherwise energized (i.e., cauterization, burning through the material, etc.) to effect the material or object that it is contacting. In such an aspect, the coiling and capture device is activated (either manually, mechanically or electromechanically through another tube or scope) to loop around material and activate a further device associated with the capture device.

In a still further aspect, the present invention relates to a self-coiling fastener or attachment clip comprising a hollow compression member and a tensioning member described above. The tensioning member is attached at, or operably connected to, the distal end of the compression member. The proximal end of the tensioning member is then tensioned, such as by pulling it through the compression member, while restraining the proximal end of the compression member. This results in one side of the compression member being deformed to form a curve or loop.

The attachment clip produced above can then retain its shape by the permanent deformation of the material produced above comprising the compression member. Alternatively, when the desired deformation has occurred, the tensioning member can be fixed or secured to the compression member. Accordingly, the attachment clip can retain its shape by the tension produced by the secured tensioning member, by permanent deformation of the material of the compression member, or some combination of the two.

This aspect of the invention can also be used to fix or join multiple objects, materials or tissue to each other. Such a self-coiling attachment clip has particular applications in the fields of construction, manufacturing, equipment maintenance, complex motion, garments, hobbies and novelty items, medicine, etc.

In a related aspect, the above-described attachment clip can be delivered and/or located by means of a deployment device, which by way of example and not limitation, may include sleeves, tubes, hoses or catheters. In one such embodiment the compression member has an inner channel for an inner tensioning member. The distal end of the tensioning member is affixed to a puncturing or piercing needle that has a diameter greater than the diameter of the inner channel of the compression member. When such a needle is deployed through a deployment device, the needle is used to puncture the target material and the inner tensioning member is used to pull the needle back towards the compression member, and the compression member deforms and compresses against and/or into the target material.

Alternatively, the present invention relates to a self-coiling attachment clip that is designed to mimic the shape of a needle and may have a tip that allows the user to puncture the material. The clip has a tensioning cable that may mimic traditional joining threads or other material.

The above-described aspects can also be utilized in a deployment device with multiple combinations of puncturing needles and attachment clips. Further, these aspects can be embodied in a single or multi-tube configuration. Moreover, these aspects also relate to a delivery/locating system with one or more separate puncturing needles and clips that can be advanced or withdrawn as needed.

Furthermore, by varying the structural characteristics of the compression member of the above-described device, the spacing of features, the shapes and patterns formed, and complex shapes other than simple curves or circular coils can be formed. This allows the fasteners, attachment clips, etc., to be used in ways that competing clips, fasteners, clamps, cutters, snares, and staples, cannot.

In still another aspect, the present invention relates to use of the compression and tensioning members described above to create structures beyond a simple curve or coil for attachment/suturing. The compression member with one or more tensioning members can be used to create cylindrical-like structures or continuous corkscrew-shaped fasteners. Similarly, custom fastener length, multiple coils and multiple sizes are also possible. Additionally, as a result of its compactness (given that it can be delivered in a linear form initially), it can be delivered in small spaces from one side to fasten a material where conventional fasteners cannot due to size limitations, etc.

In another additional aspect, the present invention concerns a material-eluting, self-coiling fastener or attachment clip. In such an embodiment, the compression member and/or the tensioning member may contain or be coated with an adhesive, chemical, materials with specifically desired magnetic or electrical properties, pharmaceuticals or other agent(s) that promote attachment, sealing or some other desired effect.

In an additional further aspect, the present invention is directed to a self-coiling fastener, attachment clip, clamp, cutter, snare, etc., comprising a compression member and a tensioning member, wherein indices concerning the direction the orientation are also included. In certain applications, it may be important to know and control, prior to application of the fastener, clip, clamp, cutter or snare, etc., the direction the compression member of the device, will deform or curl under tension. This can be managed and controlled through a number of apparatuses including, but not limited to: a tensioning cable feature such as a marking, a notch, a bump; an applicator feature such that the applicator indicates the orientation of the clip; an applicator feature that forces the clip to exit the applicator in a specific orientation; and, a preformed initial shape of clip (prior to tensioning) that indicates attachment clip orientation (for example, the clip could be curved such that the concave side indicates the coiling direction).

In another aspect of the present invention, a device capable of forming a substantially circular configuration is provided. The device includes an outer compression member and an inner tensioning member, both having proximal and distal ends. The tensioning member is at least partially disposed within the compression member. Various types of attachment means allow the distal end of the tensioning member to selectively communicate with the distal end of the compression member to produce the deformation of the compression member desired.

In a further aspect, a method for fastening material includes providing material to be attached and positioning at least a portion of a device, including a tensioning member at least partially disposed in a compression member, in a fastening relationship with a first portion of the material. The compression member is partially secured and the device is partially deformed by applying tension with the tensioning member to compress the compression member. At least a portion of the device is then placed in fastening relationship with a second portion of the material and the fastener is more fully deformed by further activation (i.e., pulling) of the tensioning member. This brings the material together and creates a knot-like structure.

In an additional aspect, a method for manipulating a fastener in a confined space includes inserting a fastener, including a compression member with a proximal end and a distal end and a tensioning member at least partially disposed within the compression member and including a proximal and a distal end, into the confined space. The proximal end of the compression member is partially secured and the surgical device is deformed to a predetermined configuration by tensioning or pulling the proximal end of the tensioning member. Other manipulations of the fastener may include procedures such as the snaring of an object, cauterization and formation of a structure, cutting or clamping, in the confined space.

The advantages and benefits of the present invention will become apparent to those of ordinary skill in the art upon reading and understanding the following detailed description of the preferred embodiments.

BRIEF DESCRIPTION OF THE DRAWINGS

The invention may take form in various components and arrangements of components, and in various steps and arrangements of steps. The drawings, in which like reference numerals denote like components throughout the several views, are only for purposes of illustrating preferred embodiments and are not to be construed as limiting the invention.

FIG. 9 is a side view of an exemplary fastener apparatus in accordance with the present invention, with different compression features;

FIG. 10 is a perspective side view of the exemplary fastener apparatus of FIG. 9 in a semi-compressed state;

FIG. 17-A is a side view of an exemplary fastener apparatus in accordance with the present invention.

FIGS. 17-B to 17-G are alternative embodiments in cross-section of FIG. 17-A at line A-A.

FIG. 18 is a side view of the fastener apparatus of FIG. 17 in a fully deployed state.

FIG. 19-A is a side view of a portion of an exemplary fastener apparatus in accordance with the present invention.

FIG. 19-B is a side view of the fastener apparatus of FIG. 19-A in the process of deployment.

FIG. 20 is an exemplary alternative configuration of the fastener apparatus of FIG. 19-A.

FIG. 21 is a perspective top view of a section of the fastener apparatus of FIG. 19-A.

FIG. 22 is a perspective bottom view of a section of the fastener apparatus of FIG. 19-A.

FIG. 23 is a perspective top view of an alternative configuration of a section for the fastener apparatus of FIGS. 19-A and 19-B.

FIG. 24 is a side view of an exemplary fastener apparatus of the present invention deployed in a helical shape in an application fastening a device to a body.

FIG. 25 is a side view of an exemplary fastener apparatus of the present invention deployed in a helical shape in an application expanding or supporting the inside of a tubular structure.

FIG. 26 is a side view of an exemplary fastener apparatus of the present invention deployed in a helical shape in an application plugging the inside of a tubular structure.

FIG. 27 is a side view of an exemplary fastener apparatus of the present invention deployed in a helical shape in an application clamping and occluding a tubular structure.

FIG. 32 is a side view of an exemplary fastener of the present invention in an application having a plurality of devices supporting a membrane.

FIG. 33-A is a side view of an exemplary fastener of the present invention in an application having a plurality of devices supporting a membrane in a deployed state producing an occlusion in a tubular structure.

FIG. 33-B is an end view of the fastener of FIG. 33-A showing the membrane in a deployed state.

FIG. 34 is a side view of an exemplary fastener of the present invention in an application snaring an organ.

DETAILED DESCRIPTION OF THE PREFERRED EMBODIMENTS

Figure 1:
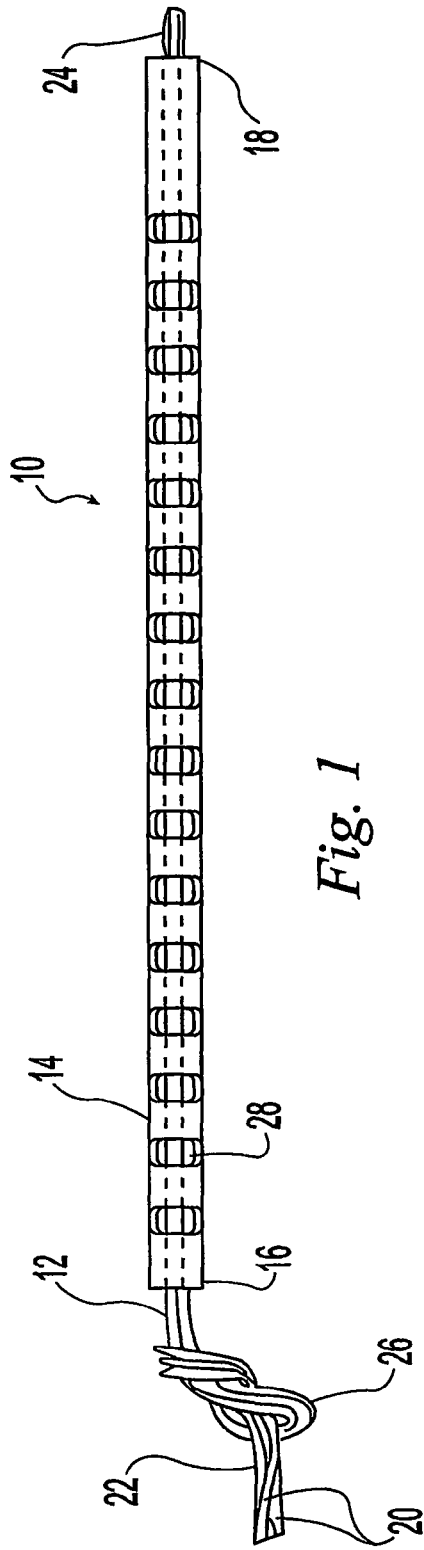
FIG. 1 is a top view of an exemplary fastener apparatus in accordance with the present invention.

Turning now to the drawings, wherein the showings are for purposes of illustrating the preferred embodiments of the invention only and not for limiting the same, FIG. 1 shows a device 10 of the present invention. The device 10 includes a tensioning member 12 that is movably disposed within a compression member 14. The compression member 14 may be a hollow tube having an inner diameter ("ID") and an outer diameter ("OD"). It is comprised of material, including without limitation metals and plastics (as will be described in greater detail below), and includes a distal end 16 and a proximal end 18.

The tensioning member 12 may be a single strand or multiple strands 20 of material, such as a metal or high strength plastic cable or rope or other materials. In some applications, the tensioning member may also be designed to include some elasticity to allow some flex in the compression member after it is compressed. The tensioning member includes a distal end 22 that corresponds to the distal end 16 of the compression member 14 and a proximal end 24 that corresponds to the proximal end 18 of the compression member 14.

A retainment or attachment member 26 is present at the distal end 22 of the tensioning member 12 to selectively hold, retain or attach the distal end 22 of the tensioning member 12 within or to the distal end 16 of the compression member 14. The retainment member 26 may take various forms, as will be shown below, and is illustrated in FIG. 1 as a simple knot in the distal end 22 of the tensioning member 12. The knot is larger than the inner diameter ID of the compression member 14 to prevent the distal end 22 of the tensioning member 12 from sliding inside of, or completely through, the compression member 14. In some applications, the tensioning member may be attached to the compression member at positions other than the distal end of the compression member to make sections of the compression member operable. In addition to the knot shown in FIG. 1, the tensioning member may be attached to the compression member by other means, including without limitation, by fasteners, welding, crimping, sealing and the like.

The proximal end 24 of the tensioning member 12 extends past the proximal end 18 of the compression member 14 to allow the proximal end 24 of the tensioning member to be grasped or operated separate from the proximal end 18 of the compression member, as will be described in detail below. In some applications, the proximal end may reside inside the compression member and be attached to an adjustment device operable by the user, including without limitation devices such as a fine screw adjustments, slides, dials, levers, gears, wheels, and the like, operable manually or electronically.

Figure 2:
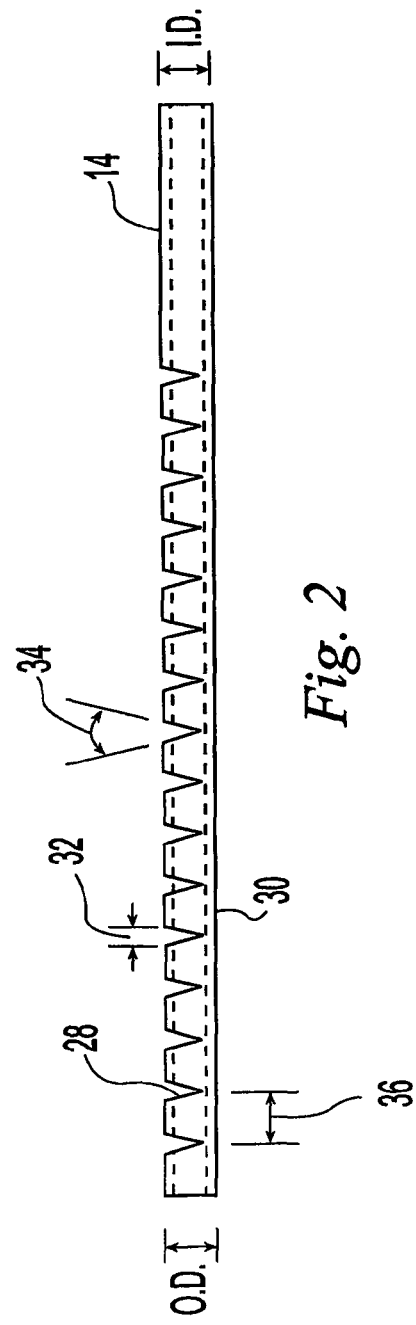
FIG. 2 is a side view of a component of the exemplary fastener apparatus of FIG. 1.
Figure 30:
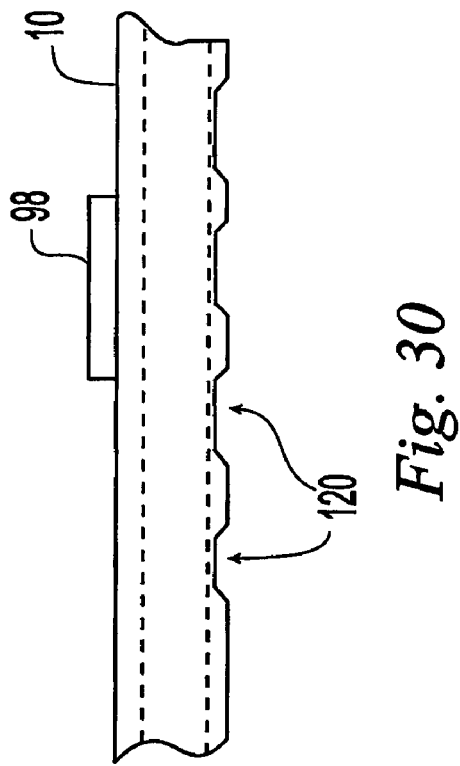
FIG. 30 is a side view of an exemplary fastener apparatus of the present invention having exemplary thinned wall sections serving as compression features, and showing an exemplary displacement detection sensor.
Figure 37:
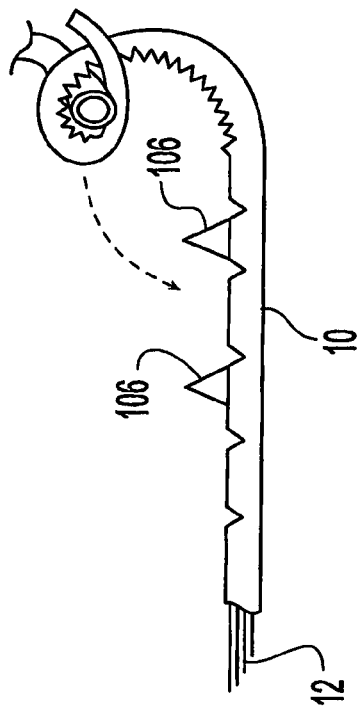
FIG. 37 is a side of an exemplary fastener of the present invention in a representative application having a cutting edge in a stage of deployment poised to cut an elongated portion of material retained by a loop of the fastener.

The compression member 14 defines flexible areas or compression features 28, such as notches, present on one side of its longitudinal axis, as shown in FIGS. 1 and 2. However, a wide variety of alternative configurations are also available. The flexible areas or compression features 28 are configured in a manner to allow for deformation of the compression member 14 in a desired direction upon the application of a compression force by the tensioning members upon activation. Alternative configurations may include compression features such as slots, weakened, etched or thinner areas 120 (FIG. 30), and opposing slanted surfaces which may run along all or part of different sides of a compression member 14, as discussed more fully below.

Turning now to FIG. 2, the compression member 14 may be a one-piece hollow tube that defines the flexible areas or compression features 28, or it may be a series of interconnected individual links with compression features 28 defined in between the individual links (see FIG. 17-A). The compression features 28 are designed to allow the compression member 14 to deform to a predetermined configuration as, for example, in FIG. 18. Preferably, the compression member is tubular and generally circular in cross-section. However, other cross-sectional configurations, such as representative geometric shapes or combinations of geometric shapes, illustratively shown in FIGS. 17-B through 17G, may be used.

Referring again to FIG. 2, a spine 30 may form a contiguous and rigid portion of the compression member 14. Additionally, the flexible areas or compression features 28 are shown as notches of a predetermined design to allow the compression member 14 to form a loop-style deformed configuration. The flexible areas or compression features 28 are present on the flexible side of the compression member.

Alternatively, as shown in FIGS. 19 through 23, the compression member may also be made of sections 90 having different sections connected serially (see FIGS. 19 and 20). In this embodiment, substantially solid sections stacked in series have compression features such as angled, beveled or protruding surfaces 86 or surface features 92, as shown illustratively in FIGS. 21 and 23 that cause the stacked sections 90 to compress to a desired shape. Advantageously, these sections 90 may be kept in alignment by an inner spine 30 running through an inner channel 31 in each section 90, or by a tensioning member 12 running through or along the stacked sections 90. Where a tensioning member 12 runs along the stacked sections, the sections 90 may optionally include a guide or loop to retain the tensioning member when it is in tension. Regardless, in either case, surface features on opposing surfaces of the sections 90, such as detents 88, and mating features, such as protruding surfaces 86, can be provided to help lock sections in a desired relationship. Such surface features also permit a user to rotate and adjust individual sections or segments to customize the shape and produce a desired configuration during use the device when compressive force is applied in accordance with the present invention. Use of one or more tensioning members extending through or along the sections make possible the application of compressive forces as desired on all or a portion of the sections 90.

Referring again to the embodiment of the invention shown in FIG. 2, the dimensions of the compression member 14, including the width 32, angle 34, spacing 36, shape and exact design of the compression features 28 will vary depending on the particular application (i.e., without an insertion device or with a deployment device, etc.) and the specific parameters (such as the size of the tensioning member and the desired shape of the compression member 14) involved.

The device 10 of the present invention may also be provided with a sleeve or material covering (not shown), which will serve to prevent pinch points and to protect against debris interfering with compression features 28.

Figure 3:
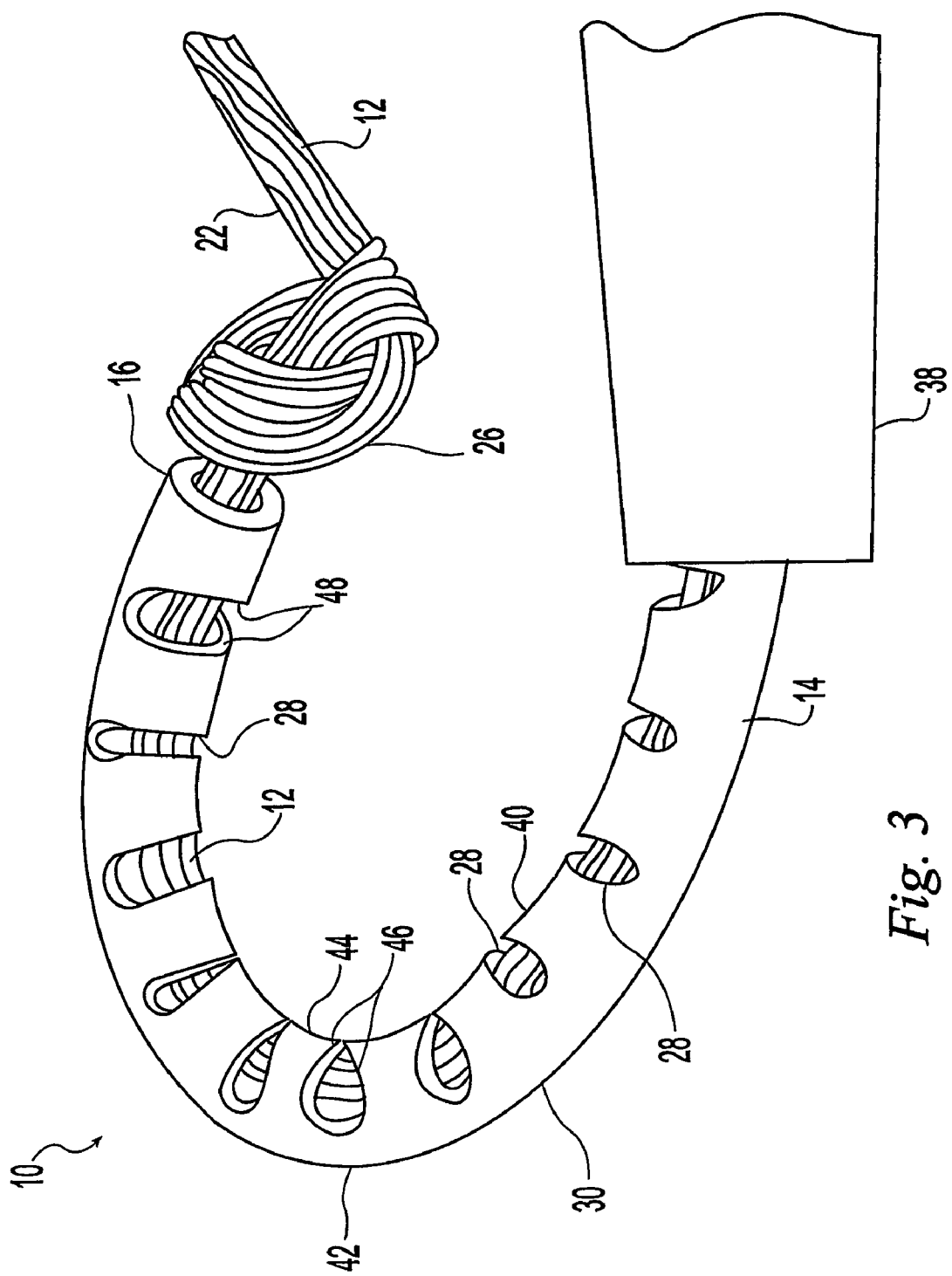
FIG. 3 is a perspective view of the exemplary fastener apparatus of FIG. 1 in a semi-activated state.

With reference to FIG. 3, deformation of the device 10 is shown. The device, as a fastener, may be used with or without an insertion device 38. For reference, use with an insertion device 38 is illustrated. The proximal end 18 (referring back to FIG. 1) of the compression member 14 is grasped and held or fixed, while the proximal end 24 (FIG. 1) of the tensioning member 12 is grasped and pulled for activation. The act of pulling the proximal end 24 of the tensioning member 12 places the inner tensioning member 12 in tension and causes the retainment or attachment means 26 to contact with and place the compression member 14 into compression. For example, the knot at the distal end 22 of the tensioning member 12 may contact the distal end 16 of the compression member 14, and with continued tension in the tensioning member 12, cause the flexible areas or compression features 28 of the compression member 14 to become compressed.

In this regard, the compression member 14 compresses about the compression features 28, which, as described above, are designed to produce a desired configuration of the compression member 14 upon deformation. The action of the distal end 22 of the tensioning member 12 on the distal end 16 of the compression member 14 continues once compression of the compression member 14 has begun, facilitated by the strong, yet flexible properties of the inner tensioning member 12. As compression of the compression member 14 continues, the design of the flexible areas or compression features 28 causes one surface 40 of the compression member 14 to be placed into compression and another surface 42 of the compression member 14, i.e., the spine 30, to be placed in tension and plastically deform. The apex of these forces may occur at a predetermined location 44, where opposing walls 46 that define the compression features 28 at the apex close upon one other, while opposing walls 48 not at the apex are still a significant distance apart.

Figure 4:
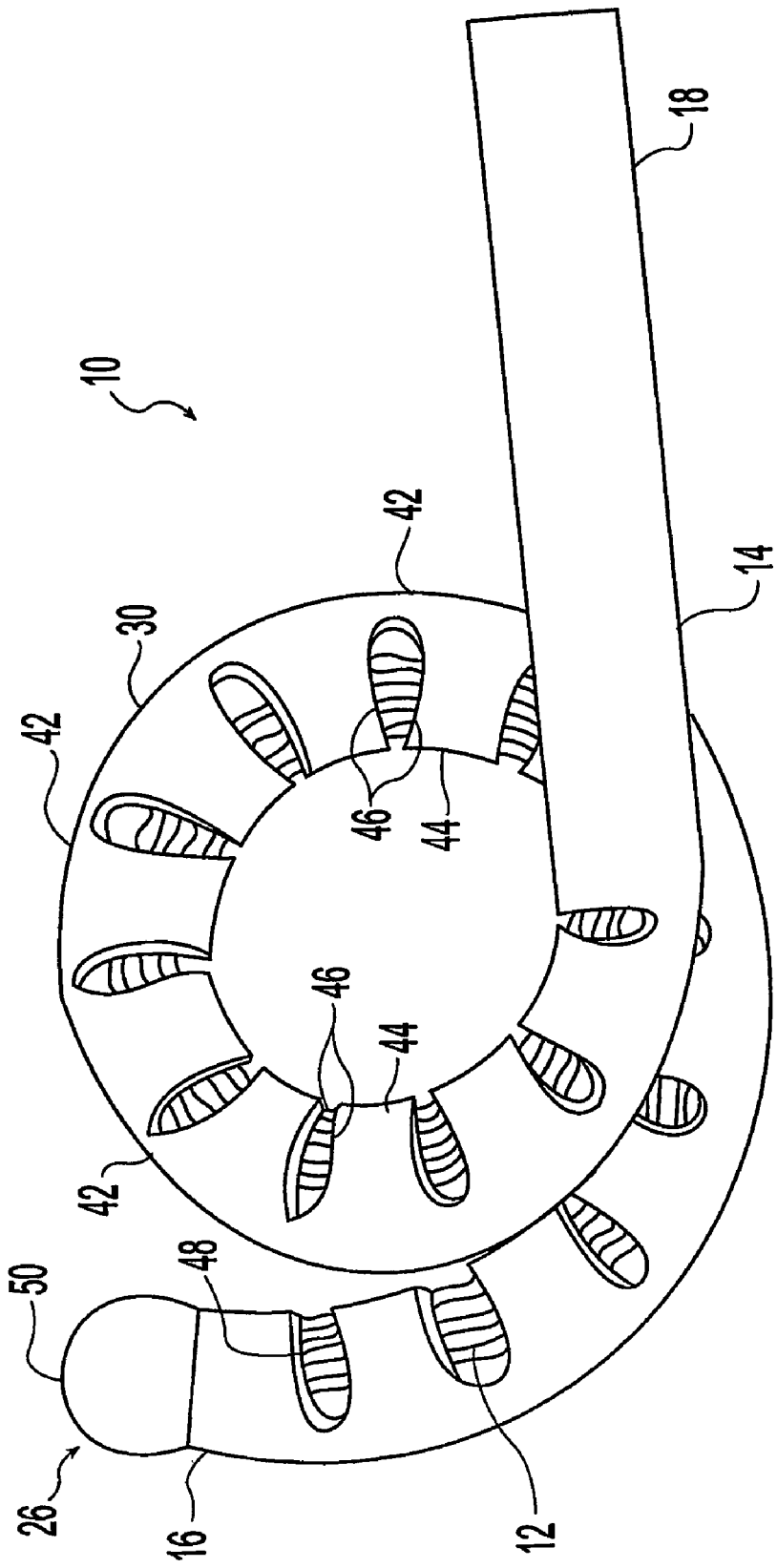
FIG. 4 is a perspective side view of the exemplary fastener apparatus of FIG. 1 in an activated state, with different attachment means.

As FIG. 4 illustrates, a substantially completely deformed fastener, shown here as a substantially closed loop, is formed with continued tension of the inner tensioning member 12 imparting compression upon the compression member 14. As mentioned above, the retainment or attachment means 26 may take several forms, including a sphere 50 in which the distal end 22 (FIG. 1) of the tensioning member 12 is fastened (such as by crimping, ultrasonic welding or other means known in the art), and which in turn contacts the distal end 16 of the compression member 14. When the fastener is in a substantially finally deformed configuration, a significant portion 44 of the compression member 14 includes the apex of the compressive forces.

When the compression member 14, and thus the fastener, has deformed to the desired configuration, the proximal end 24 of the tensioning member 12 can be attached to the proximal end 18 of the compression member 14 and any remainder of the tensioning member 12 protruding outside of the proximal end of the compression member 14 can be detached. This may be performed in a number of ways.

Figure 5:
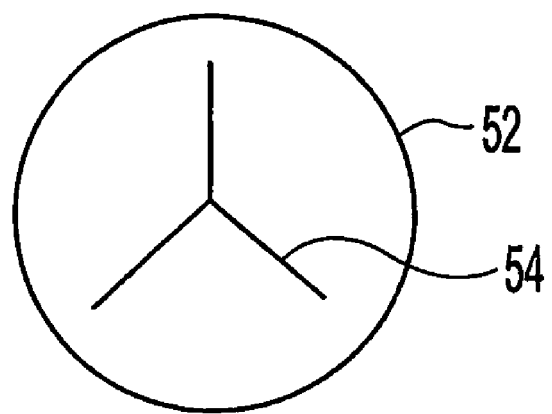
FIG. 5 is a front view of a retention device used in accordance with the present invention.
Figure 6:
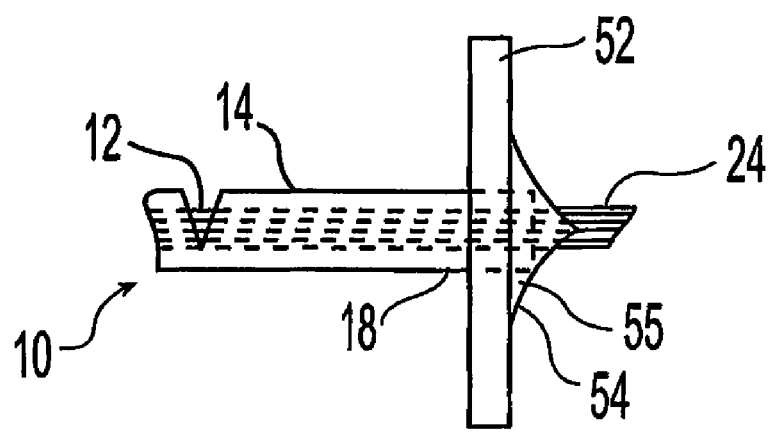
FIG. 6 is a side view of the retention device of FIG. 5 with a portion of an exemplary fastener apparatus.

For example, a unidirectional cable retention apparatus, as known in the art, may be used. Turning to FIGS. 5 and 6, a retention apparatus 52 defines slots 54. While the proximal end 18 of the compression member 14 and the proximal end 24 of the tensioning member 12 remain grasped, the tensioning member 12 is passed through the slots 54 in the retention apparatus 52, and the apparatus 52 is slid down the tensioning member 12 until it contacts the proximal end 18 of the compression member 14. Flaps 55 created by the slots 54 cooperate to create a force that causes the retention apparatus 52 to lock onto the tensioning member 12. As a result, the tensioning member 12 is held in place at the proximal end 18 of the compression member 14 by the retention apparatus 52. Any portion of the tensioning member 12 extending substantially beyond the retention apparatus 52 may then be cut and removed.

Other means of attaching the proximal end 24 of the tensioning member 12 to the proximal end 18 of the compression member 14 include crimping the proximal end 18 of the compression member 14 at the proximal end 24 of the tensioning member 12. Similarly, a separate swage fitting may be crimped on the tensioning member 12 just past the proximal end 18 of the compression member 14. Also, a wedge lock, which is a protrusion that allows the tensioning member 12 to be moved only in one direction (i.e., the direction of pulling for tension), may be used in the compression member 14 at or near the proximal end 24, or the inner diameter of the compression member 14 may be shaped to create a wedge lock. Other one-way locking apparatuses, such as cam-type devices and detent mechanisms may be employed. Moreover, the means of attachment of the tensioning member 12 to the compression member 14 at their respective proximal ends 24 and 18 may be by an ultrasonic or other type of weld, which may also be used to trim any excess portion of the tensioning member 12.

Various means are described herein to retain, temporarily, adjustably, and permanently, the inner member in tension to hold the shape of the outer member.

Once the proximal end 24 of the tensioning member 12 is attached to the proximal end 18 of the compression member 14, any one of several forces may cause the device 10 to retain its deformed shape (referring back to FIG. 4). First, attachment of the proximal end 24 of the tensioning member 12 to the proximal end 18 of the compression member 14 keeps the tensioning member 12 in tension, thus keeping the compression member 14 in its deformed position. Second, the deformation of the compression member 14 may be permanent, causing the compression member 14 to remain in its deformed position. If only this plastic deformation force is desired, the tensioning member 12 may be removed from the compression member 14 (as will be described below). Third, a combination of the tensioning member 12 in tension and plastic deformation of the compression member 14 may cooperate to keep the compression member 14, and thus the device 10, in its deformed position.

Figure 7:
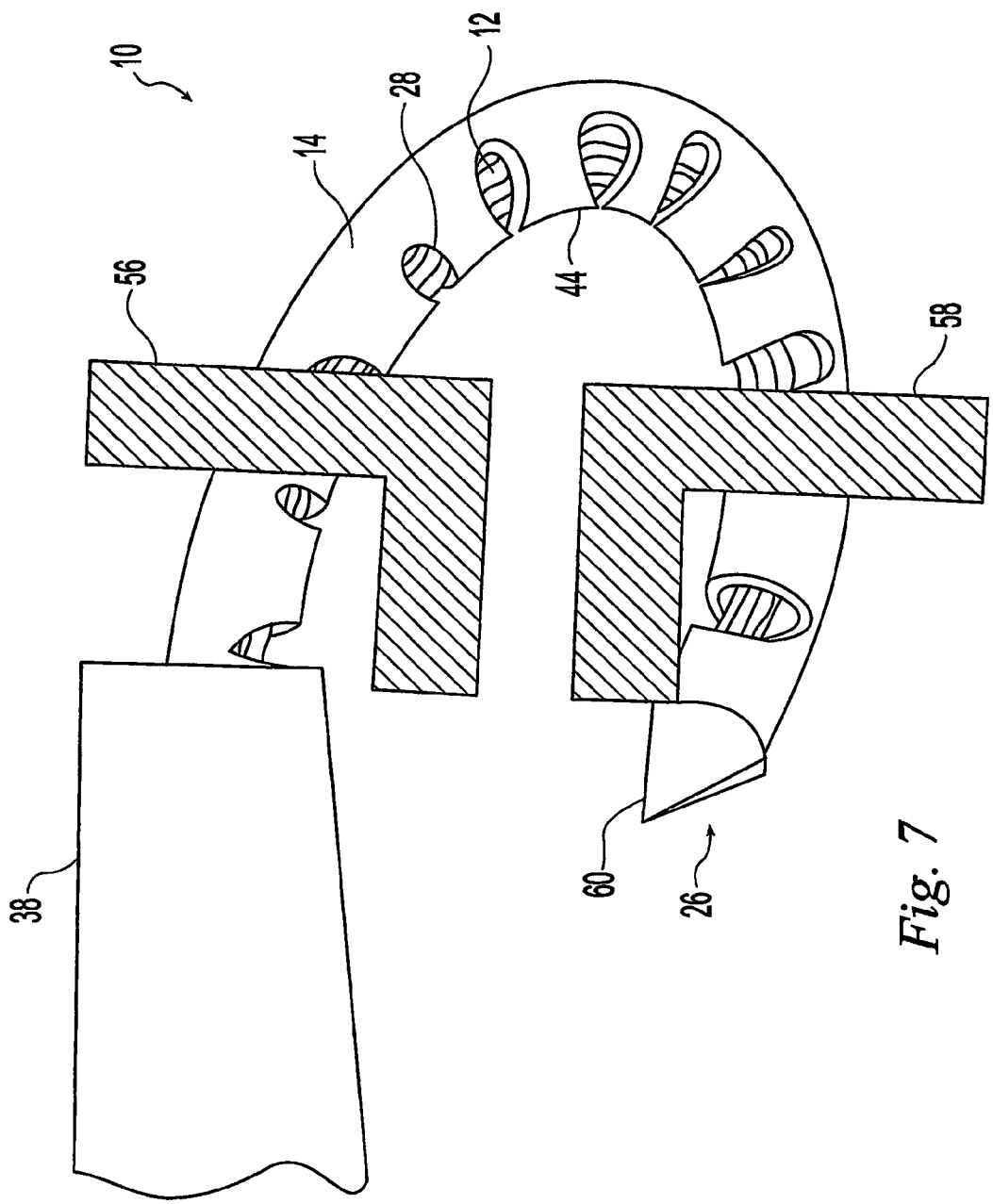
FIG. 7 is a perspective side view of the exemplary fastener apparatus of FIG. 1 in the process of being deployed in material, with different attachment means.
Figure 8:
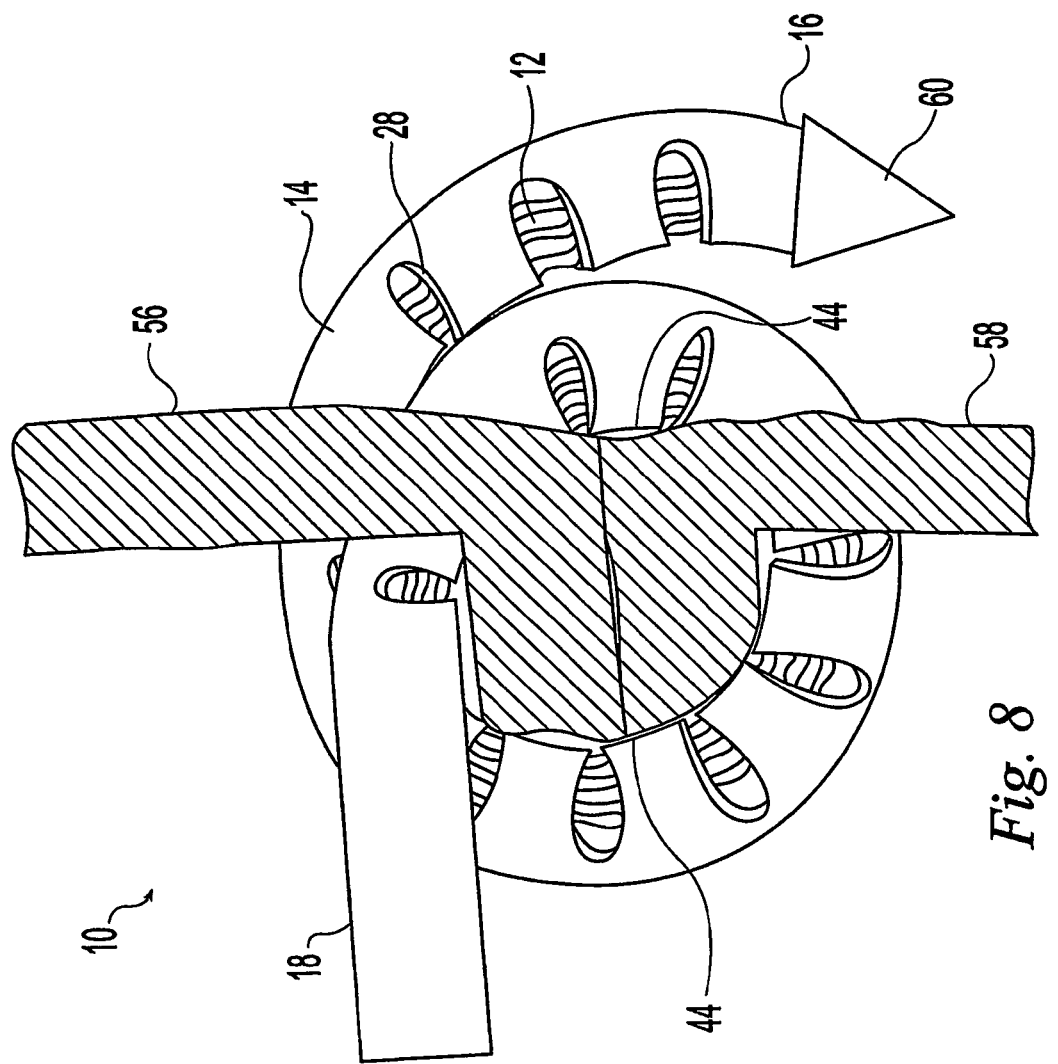
FIG. 8 is a perspective side view of the exemplary fastener apparatus of FIG. 7 in a fully deployed state.

In this manner, the formation of a strong fastener device 10 with minimal space requirements, i.e., by grasping only the proximal ends 18 and 24 of the components, is achieved. With reference to FIGS. 7 and 8, use of the fastener 10 to join disconnected materials is illustrated. A first material 56 and a second material 58 are to be joined. The fastener includes a piercing tip 60 as the retainment or attachment member 26 to attach the distal end 22 of the tensioning member 12 to the distal end 16 of the compression member 14. The piercing tip 60 allows the fastener device 10 to pierce the material 56 and 58 with minimal space and without the use of an additional needle, drill, punch or the like, or the additional step of creating an aperture, if desired. Also, if desired, the insertion device 38 may be used to deploy the fastener.

As shown in FIG. 24, at the micro-scale, this configuration of the device may be used to deploy a fastener attached to or extending from, by way of example and not limitation, a Micro-ElectroMechanical system (MEMs) device 94, monitor, lab on a chip, pharmaceutical chip, etc; or alternatively, at a larger scale, attach any known implantable device. The device 10 may provide permanent or temporary attachment of a device 94 to a specific location in a human or animal where the device 94 acts to fulfill physical, electrical, pharmaceutical or medicinal treatment purposes. As an alternative to the fastening shown in FIGS. 7 and 8, FIG. 24 illustrates that attachment may be made to a single piece of material or tissue using a loop or preferably a helical configuration of the device 10. It may also be understood from FIG. 24 that the loop or helical configuration of device 10 may be designed to encircle and thus fasten or bundle together a plurality of generally parallel or closely aligned materials.

Referring again to FIGS. 3 and 7, the compression member 14 is moved forward from the insertion device 38 to cause the piercing tip 60 to penetrate the first material 56. The compression member 14, having the tensioning member 12 disposed in its inner diameter, is moved partially through the first material 56. The proximal end of the compression member 18 (referring back to FIG. 1) is grasped and the proximal end 24 of the tensioning member 12 (FIG. 1) is pulled to cause the compression member 14 to begin to deform to a shape dictated by the compression features 28, which is shown as a loop. When the piercing tip 60 has curved to approximately 180 degrees from its insertion angle, the entire fastener is pulled in a rearward direction, causing the piercing tip 60 to penetrate the second material 58 (FIGS. 7 and 8).

Alternatively, instead of pulling the entire fastener rearwardly to engage the second material, the compression member 14 can merely be further compressed to engage the second material. Utilizing such a technique, the piercing tip 60 will then engage the second material to produce a compressed fastener.

As FIG. 8 illustrates, once the piercing tip 60 has penetrated the second material 58, the fastener device 10 may again be moved forward to allow more of the fastener to pass through the first 56 and second 58 material. The proximal end 24 of the tensioning member 12 is pulled more, causing the compression member 14 to in turn deform more and form a loop. As the loop is formed, the first 56 and second 58 materials are drawn together. The proximal end 24 of the tensioning member 12 may be pulled even more, so as to cause the piercing tip 60 to pass through the first material 56 a second time. When the first 56 and second 58 materials are secured by the fastener 10 in the desired position, the proximal end 24 of the tensioning member 12 is attached to the proximal end 18 of the compression member 14, as described above, and any remainder of the tensioning member 12 protruding outside of the proximal end of the compression member 14 may be optionally removed or cut off. It is important to note that the fastener may secure two materials 56 and 58 together, or it may secure one material 56 to some other object, or may secure two portions of the same material, as desired.

Turning to FIGS. 9 and 10, the fastener device 10 may include various forms of compression features 28. These features 28 may include notches, as previously described, or corrugations 62. The corrugations 62 compress (FIGS. 10 and 31) to facilitate the formation of a pre-designed configuration upon compression of the compression member 14. Also, the flexible areas or compression features 28 may include the use of a thinner wall 96 (FIG. 30) than the remainder of the compression member 14, again leading to the formation of a pre-designed configuration upon compression. The considerations described above regarding the compression features 28 apply to all of the forms that are utilized.

Various means are described herein to compress the compression member. For example, a bladder (not shown) in the inner member may be expanded or contracted to cause motion of the outer member, or piezoelectric elements (not shown) may be used on the outer or inner member to create motion. Similarly, bi-metallic or expansion differential of materials for temperature based bending may be utilized. A collection of sections 90 with surface features, such as protruding surfaces 86 or posts to adjust which way the device bends (i.e. dynamic determination of bending pattern). See FIGS. 19 and 20. As well, a collection of multiple discs with multiple pins could allow independent control of larger segments of the fastener. Similarly, multiple inner tension members connected to individual segments of the device could also be used for control of separate sections 90 or segments or for ones of a group of devices 10 (FIG. 33-A). Tension members can also be configured to provide for stronger forces, for applications such as those shown illustratively in FIGS. 18, 25, 26, 27, 35, 36 and 37, or tuned to special needs of an application, such as illustratively shown in FIGS. 8, 33, 34, 38, 39 and 40.

When the fastener device 10 is used without an insertion device 38, the fastener may be inserted in alternative manners. For example, the proximal end 18 (referring back to FIG. 1) of the compression member 14 may be held by a clamp or pliers or similar device to control the pushing of the fastener 10 through material. A piercing tip 60 (FIG. 7) may be used to allow the fastener to pass through the material. When deformation is desired, a second tool may be used to grasp the proximal end 24 (FIG. 1) of the tensioning member 12 and pull it to deform the compression member 14.

Figure 11:
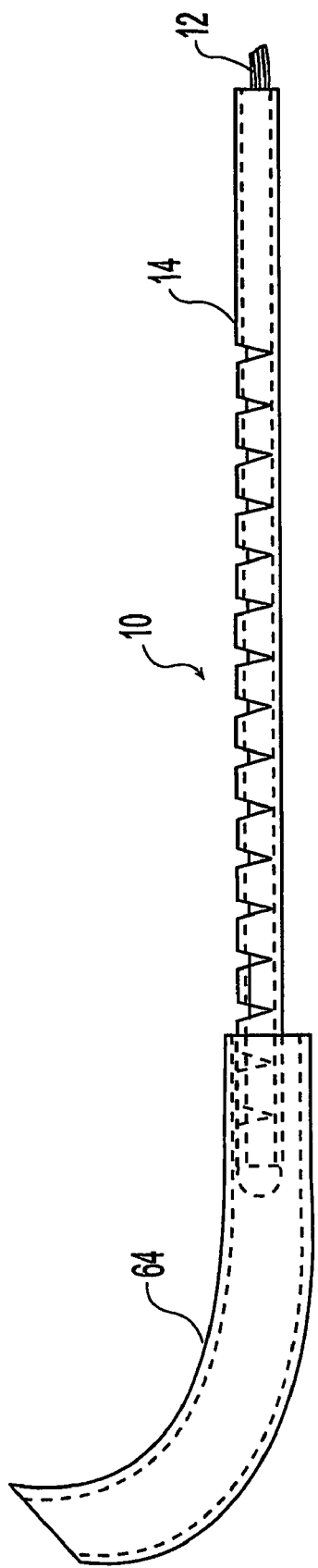
FIG. 11 is a side view of an exemplary fastener apparatus in accordance with the present invention with curved hypodermic needle means of deployment.

As an alternative to the deployment of the fastener device 10 without an insertion device, different types of devices may be used. For example, a straight, hollow tube structure 38 as shown in FIGS. 3 and 7 above may serve to position and allow control of the fastener. This tube structure 38 may be a needle, nail, punch, drill, torch or similar tool that punctures the material for the fastener, and through which the fastener is then inserted to the material. In addition, a curved tool 64, such as a hypodermic needle, as illustrated in FIG. 11 and useful in a medical application, may be used to insert the fastener. A curved tool 64 would assist in the placement, control and deformation of the fastener, as it forms a portion of a possible configuration of the compressed fastener, i.e., a loop.

Figure 12:
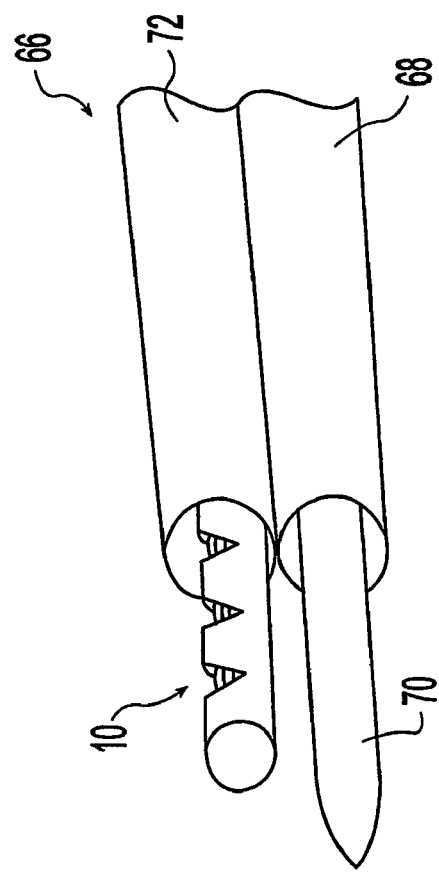
FIG. 12 is a perspective view of an exemplary fastener apparatus in accordance with the present invention with a double tube means of deployment.
Figure 13:
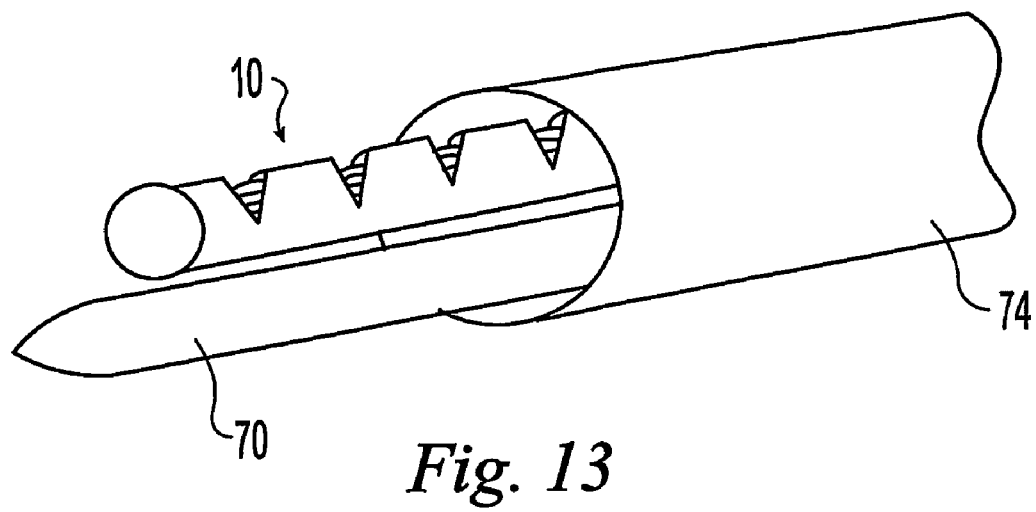
FIG. 13 is a perspective view of an exemplary fastener apparatus in accordance with the present invention with a single tube means of deployment.

With reference to FIGS. 12 and 13, other insertion devices may include a double tube system 66, wherein a first tube 68 houses a puncturing needle 70 that pierces the material for the fastener. When the material is pierced, the needle 70 may be drawn back into the first tube 68 and the fastener 10 then inserted through the punctured material. The fastener 10 is controlled via a second tube 72 that may be connected to the first tube 70. As shown in FIG. 13, alternatively, a single tube system 74 may house both the puncturing needle 70 and the fastener 10.

Figure 14:
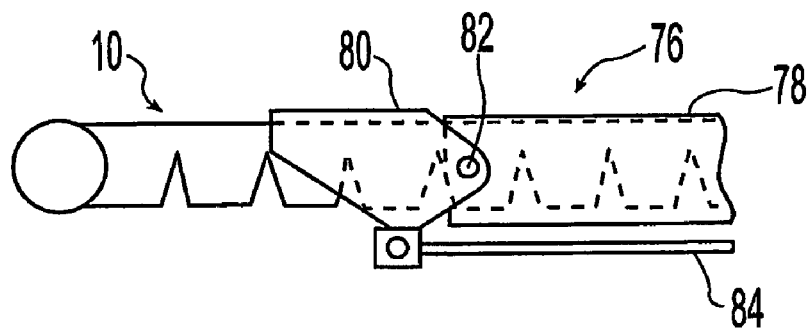
FIG. 14 is a side view of an exemplary fastener apparatus in accordance with the present invention with a hinged advancer means of deployment.
Figure 15:
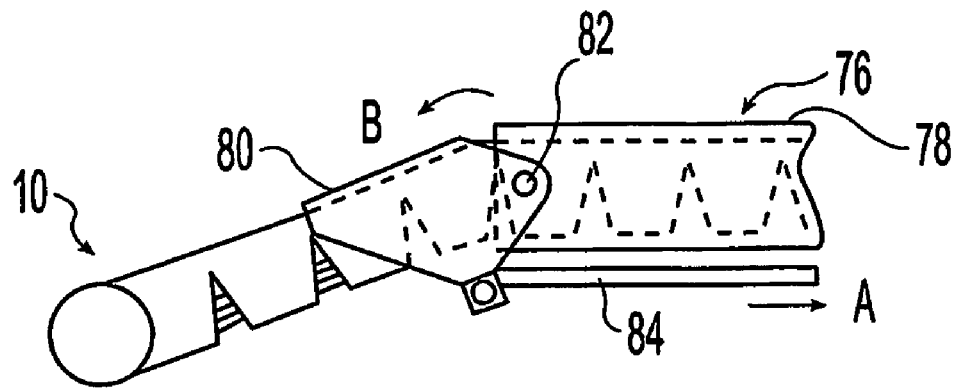
FIG. 15 is a side view of the fastener apparatus and hinged advancer means of deployment of FIG. 14 at a phase in the process of deployment.
Figure 16:
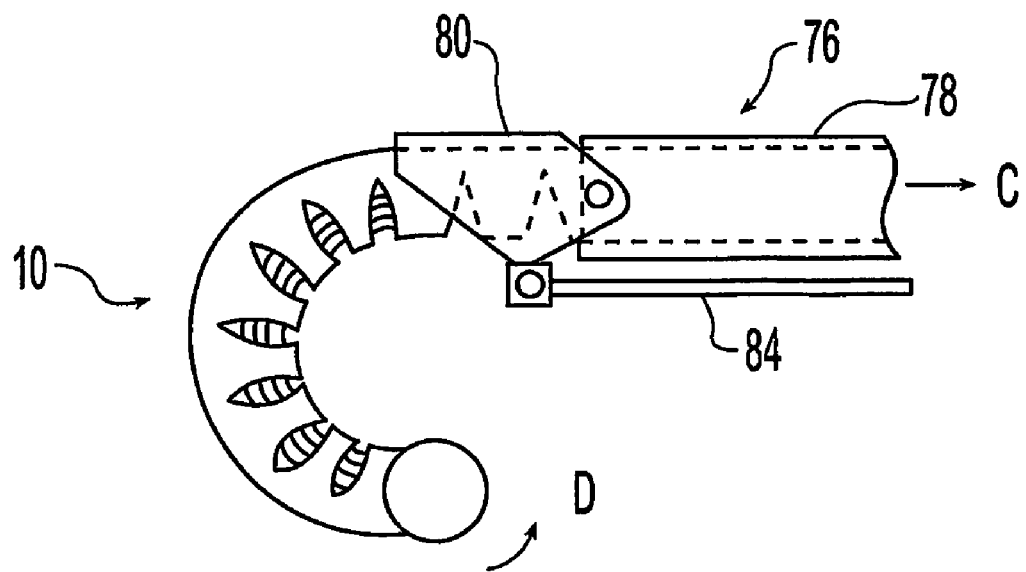
FIG. 16 is a side view of the fastener apparatus and hinged advancer means of deployment of FIG. 14 at another phase in the process of deployment.

Turning to FIGS. 14-16, a hinged applicator 76 may also be used as an insertion device. The applicator 76 includes a body 78 that removably houses the fastener, a hinged tip 80 connected to the body 78 at a hinge point 82 and an activation lever 84 for the hinged tip 80. The fastener may be fed through the body 78 of the applicator 76 in incremental fashion, as shown in FIG. 14, thus remaining substantially straight.

When deformation of the fastener is desired, FIG. 15, the hinged tip 80 may be activated by moving the lever 84 in the direction of the arrow A. The tip 80 pivots in the direction of the second arrow B, thus assisting the tensioning member 12 (referring back to FIG. 1) in compressing the compression member 14 (FIG. 1). Complete deformation of the fastener, FIG. 16, is accomplished by pulling the tensioning member 12 in the direction of the third arrow C (as described above), causing the distal end of the fastener to move in the direction of the fourth arrow D, forming the predetermined shape.

Any insertion device may be equipped to insert multiple loads of fasteners, i.e., one fastener after another. Control over the insertion of the fastener and the deformation of the fastener to the final predetermined shape may be mechanical, electrical, or electro-mechanical. For example, the fastener may be inserted into a cavity through a catheter or scope, involving both electrical imaging and sensing and mechanical dictation of movement. In addition, insertion of the device 10 may be combined with lighting or imaging, such as fiber optic or light-emitting diode (LED) means 96 located at the end or along the device 10 (FIG. 25). As well, a device with multiple tubes 68, 72 such as shown in FIG. 12, with or without additional tools noted above, may be used to guide an adjoining tube to an individual target in a confined space and provide or remove a desired material or fluid for an application through the adjoining tube. For example, in medical applications tissue, or a fluid such as oxygen, water, saline solution, stimuli sensitive materials (such as those that gel upon changes in temperature, pH, or electrical conditions), body fluids or medicaments may be provided or removed through the adjoining tube. Further, the adjoining tube may be used to supply vacuum, fluids or power to an additional tool being used contemporaneously with or requiring supply from the device 10. Using such devices permits the device of the present invention to exhibit added functionality.

The particular devices used to insert and/or control the device 10 may include features to indicate the orientation and/or depth of insertion of the deformed device 10 to allow for predictability of motion. Such features include a marking on the insertion device indicating the direction of curl or deformation or an insertion device that allows deformation in only one direction. Moreover, the device 10 may include features to indicate its final deformed shape, such as a slight initial deformation indicating the final shape and direction of curl, or a marking on a component of the device 10, such as on the proximal end 24 of the tensioning member 12, indicating the direction of deformation. Alternatively, the device could include other means for indicating electronically that at least a portion of the outer compression element has been bent. For example, piezoelectric materials, load cells, stress or strain gauges, i.e. displacement detection sensors 98 (FIG. 30) can be added to the outer compression member or inner tensioning member to detect and transmit signals relating to where, when and how much deformation is experienced in the device 10, or whether a configuration which might be defined as "closed" is reached. The insertion and controlling devices for the device 10 may also include means to indicate the tension of the tensioning member 12 in the compression member 14, thus showing the amount of deformation in the device 10 so that it can be manipulated accordingly.

In some applications, fine control of pressure applied by the device 10 is desirable, and feedback to the user through gauges, readouts or tactile sensation can be provided. Pressure sensors placed at the distal end or along the surfaces of the compression member in contact with a target object or material can be connected back wirelessly or through the device 10 to the proximal end of, or user contact point with, the device 10; or alternately to a separate readout.

Figure 29:
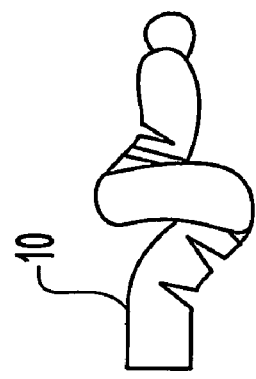
FIG. 29 is a side view of an exemplary fastener apparatus of the present invention having compressions features at different locations to form a knot-like structure.

Thus, the device 10 of the invention may be deformed along a pre-determined axis to a desired configuration. Specific, controllable loop-type shapes may be achieved, including circles, ellipses (FIG. 18), helixes 100 (FIGS. 24-27, and multiple-loop configurations. As well, the device may be designed with compression features that are positioned to permit some randomness in the final shape, where the application simply calls for the compression member to end up in a final configuration which is non-linear, or tightly and randomly curled, as illustratively shown in FIG. 29. The length of the device 10, the number of coils formed by the device 10, as well as the size of each coil formed may be dictated through the design of aspects such as the compression features 28, described in detail above. A customizable structure that may be controlled from a single area, i.e., a proximal end of the device 10, along a single plane of movement is achievable. As a result, the insertion depth and the curl of the device 10 can be controlled simultaneously in a confined space.

As noted above, the device 10 may be permanent or removable. To be removable, the tensioning member 12 may be configured to break free from the compression member 14 at an elevated force level, i.e., a force significantly greater than that necessary to deform the device 10 to the desired configuration. In such an instance, the compression member 14 may be designed to deform somewhat elastically, to spring at least somewhat open for easier removal, as described below. In applications where devices 10 may be located on a permanent or long-term basis, the device may further include an RF tag as known in the art, to enable location for replacement or removal.

Of course, applications other than fastening and attachment of materials are possible with the present invention. For example, the device 10 may be used as a self-coiling snare 102, as in FIG. 34, to grasp materials, organs (as shown) or tissues and move them as needed in confined spaces. In such applications as a snare 102, the surface of the snare may include adhesives, tackifiers, flexible materials, elastic or shock absorptive materials, textured surfaces and combinations thereof to enhance the interface of the snare 102 with sensitive tissues and materials.

When used in attachment applications in confined spaces, rather than loop over an end of an object to be grabbed, as done by devices of the prior art, the device 10 can be inserted using a minimum of space as a straight element beside the object, and be formed into a loop around a portion of the object, as in FIGS. 24, 26 and 27. Thus, the object can be grasped and moved by the device 10 without the need for locating an end of the object. Similarly, the device can be placed in a fastening relationship near a plurality of objects, and used to grasp or tie together a bundle of objects, as illustratively shown in FIG. 35.

Figure 36:
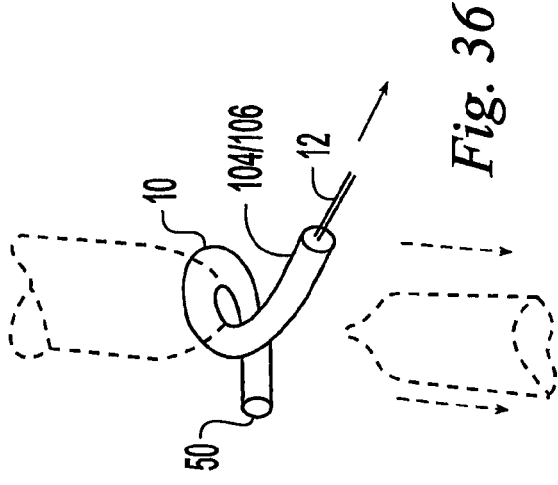
FIG. 36 is a perspective view of an exemplary fastener of the present invention in a representative application having a cutting edge or heated edge, deployed to cut or seal an elongated portion of material.
Figure 35:
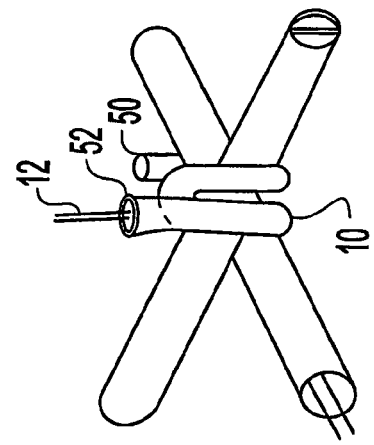
FIG. 35 is a perspective view of an exemplary fastener of the present invention in a representative application, deployed to connect two reinforcing rods.

The device 10 may also incorporate systems known in the art that allow it to be heated or otherwise energized to burn or seal materials, such as a heated edge 104 representatively shown in FIG. 36. A representative heated edge 104 may be created by various means, including heating elements on a plurality of segments or sections of the device, or by a heated wire positioned externally in like manner as the tension member 12 shown in FIG. 20, or a flexible heating element accompanying the device 10 positioned to contact a target material when the device 10 is deployed Where the compression member is be provided with an outer surface feature that includes a cutting edge 106, the cutting edge 106 may be variously designed to be positionable to grip and excise, scrape or cut a portion of material in a place where access is limited or direct human contact is not desired, such as with biological, chemical or nuclear materials, In such burning or cutting applications, the device 10 may be made of any suitable material, but is preferably made of spring metal, as described below, to allow it to loop around objects, perform a burning, cutting or sealing operation, un-loop and be removed (see also FIG. 37). As well, the device 10 may also incorporate a known cooling device, such as a thermoelectric device.

Moreover, as shown in FIG. 25, the device 10 may be deformed to a helical configuration 100 or similar specific shape and then used as a structure or formation, such as a reinforcement device inside a tube or conduit, or alternatively may be inserted linearly in such an application and deployed. In this regard, the device 10 of the present invention is also understood to be a force multiplier, permitting the linear force of tensioning to be translated into lateral motion, with a degree of multiplication in lateral force being a matter of detailed design of the compression and tensioning members.

The device 10 and its components may be of any material compatible with desired applications, including various metals, alloys, polymers, ceramics or combinations thereof. Specialty metals, by way of example and not limitation, may include for medical applications stainless steel, titanium or alloys thereof such as Nitinol, and other medically accepted metals. As well, device 10 and at least some of its components may be made of dissolvable, biodegradable or resorbable materials. For example, in some applications the piercing tip 60 or cutting edge may be of a biodegradable material so that sharp edges are degraded within a short period of time after use, reducing the possibility of unintended further piercing or cutting of material.

It is also possible to include a spring-type material for components such as the compression member 14. In such an instance, the compression member 14 may only elastically deform and remain in its deformed shape due to the tension of the tensioning member 12. When the force of the tensioning member 12 is removed, the fastener may substantially resume its original configuration for removal. In additional to more traditional spring-type materials, other materials, such as Nitinol™ may be used to return the device to its original shape. Alternatively, a pre-shaped device made of Nitinol may be used to assist in predetermining the desired shape of the fastener in use, so that the conditions of use, such as temperature, help support its function.

Figure 31:
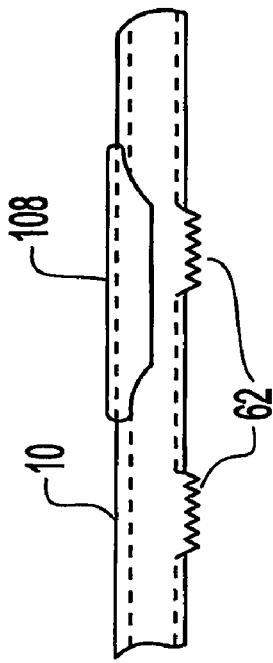
FIG. 31 is a side view of an exemplary fastener apparatus of the present invention having exemplary bellowed wall sections serving as compression features, and showing an exemplary coating.
Figure 28:
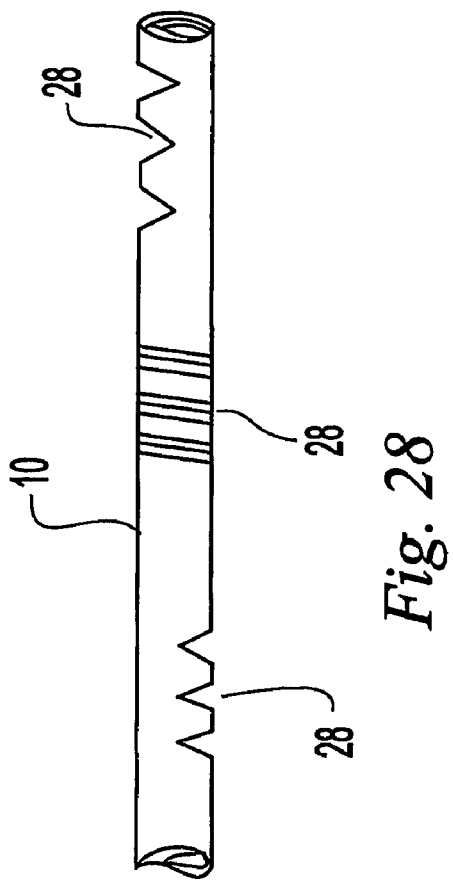
FIG. 28 is a side view of an exemplary fastener apparatus of the present invention having compression features at different locations on the device to produce different shapes.

In addition, the materials used for the device 10 may be coated with other materials to provide added functionality to the device. As shown in FIG. 31, coatings 108 include by way of example and not limitation, adhesives; pliable, cushioned or absorbent materials; or magnetic materials. In addition, functional surfaces may be provide on or connected to the device 10, such as flattened surfaces shaped surfaces; heated or cooled surfaces; fixed or retractable roughened surfaces; fixed surface features or retractable surface features, including without limitation textures, bumps, pins or the like or interlocking profiles, operable via fluid (liquid or gas) supplied to a bladder or expandable volume, or by electrical or mechanical action; may be attached or applied to device 10 to enhance snaring, gripping, stabilizing, cutting, burning, fastening, separating or spreading. Additional coating agents or surface treatments to be applied to an object may be carried by the device 10 in accordance with the needs to snare, grip, stabilize, cut, burn, fasten, separate, spread or like activities enabled by the device to achieve some other desired effect.

Further, the device may include a plurality of frangible containers 110 (FIG. 38) or pockets that rupture upon bending of the compression member 14 that release a substance to be applied to achieve a desired effect, such as those disclosed herein. Such substances may be coatings, sealants, adhesives, chemical agents to soften or harden material, and the like.

Figure 38:
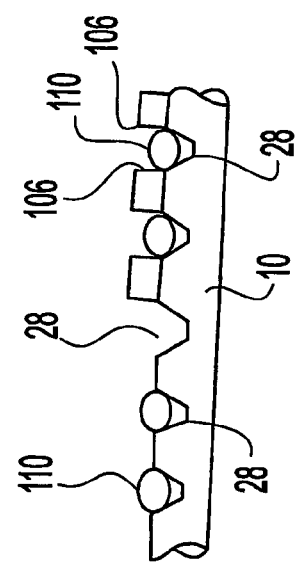
FIG. 38 is a side view of an exemplary fastener of the present invention in a representative application illustrating frangible containers and a representative detail configuration of cutting edges of FIG. 36.

Still referring to FIG. 38, In medical applications, coatings 108 or frangible containers 110 or pockets might also include pharmaceuticals, other biologically active ingredients or natural agents to promote homeostasis or other desired effects in humans, plants or animals, antibiotics, anti-inflammatory drugs, hormones, cells, DNA, medicaments, pharmaceutical active ingredients, chemicals, nuclear materials and combinations thereof. The frangible container 110 itself may also be comprised of materials desired to be delivered to the point of use by the device 10.

The device of the present invention may be applied variously in a wide range of product applications. As a fastener, the device may be designed to reach a predetermined configuration, such as an oval or link as seen in FIG. 18, that serves as a temporary connector link, or with sufficient articulation to fit around objects such as reinforcing rods (shown in FIG. 35) to serve as a permanent tie. As well, in various configurations, including a helical shape, it may serve in fastener as well as gripping applications as wide-ranging as a remote actuating device, temporary clamp for use in construction or other trades to a gripping device for the elderly, or like uses.

In an alternative configuration of the oval shaped device 10 of FIG. 18, although not shown in FIG. 18, the tensioning member 12 may include two strands, the distal ends of which are connected to each opposing end of the device, and the proximal ends of which exit the device 10 generally at its mid-point. In such an alternative configuration, the compression features 28 of the device 10 may also be designed to produce a configuration in which the opposing ends of device 10 move together to function in clamping, cutting and similar applications.

As well, although also not shown on the illustrative device 10 of FIG. 18, compression features 28 may be provided so that the opposing ends of the device 10 may be configured to form loops that overlap and interlock to form a complete link, as may be desired in some product applications.

In medical applications, the device 10, in various configurations under compression, including but not limited to generally oval, circular or helical configurations, may be used to suture or clamp tissues together, or to temporarily move, lasso, stabilize, separate or retract tissues or organs as needed during surgery. The various features of the invention, such as elasticity in the tensioning member and surface treatments or features previously described may be advantageously used to enhance contact with tissues for these uses. Some examples of particular interest include using the device 10 (or a plurality of devices 10) as a finger 112 to assist in the retraction of tissues for minimally invasive as well as conventional surgery (FIG. 39); using the device 10 in a loop or helical configuration to provide a low impact heart lasso or snare 102 for retraction of a beating heart (FIG. 34); or to surround the stomach as a band to reduce stomach volume; using the device 10 in a helical configuration 100 or similar specific shape as: a stent inside a vein or artery, or to provide vascular reinforcement during stent replacement, or to temporarily open an airway or other collapsed, inflamed or blocked tissue or gut, or to temporarily expand tissue in a vessel, tube or gut to expose an area for inspection, sampling, biopsy, analysis or surgery. The helical configuration 100 may also be used to externally surround and reinforce an aneurysm. The device 10 may also be used to provide occlusions, such as using the device 10 in a knot-like configuration (FIG. 29) or in a helical configuration alone (FIG. 27) or combination with a membrane 114 (FIGS. 32-34) on its distal end to temporarily or permanent occlude a vessel, tube, vein or artery, such as may be desirable during surgery or for temporary human or animal sterilization. In applications where an occlusion is desired, the device 10 may also be used in a generally circular or helical configuration to externally clamp closed a vessel, tube vein or artery (FIG. 27). Alternately, to form an occlusion the device 10 can be used in combination with a plug 116, wadding or the like (FIG. 26) inserted in a vessel, tube, vein or artery so that the device 10 can deploy in a generally circular, helical or other like form to clamp around the plug location and provide an occlusion.

Figure 39:
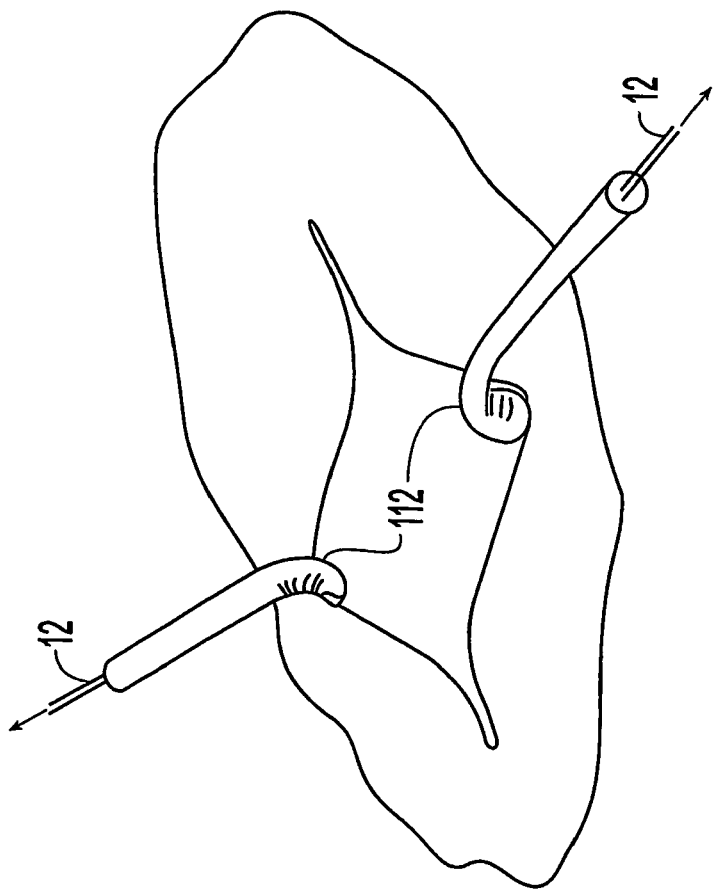
FIG. 39 is a perspective view of an exemplary fastener of the present invention in a representative application as fingers separating and holding tissues back from an incision.

Depending upon the particular application, multiple devices 10 may be used approximately simultaneously (FIGS. 33, 39). For example, an insertion device or multiple tube system, as shown in FIGS. 3 and 12, respectively, may be capable of introducing more than one puncturing needle 70 and/or device 10 at about the same time, so that multiple punctures could be made and multiple fasteners could be deployed. In addition, a first finger may be nested inside longitudinally another second finger, and positioned to slide outward from the end of the second finger, after which the first and second fingers may be selectively deployed, thus, effectively extending the reach of device 10.

Deployment of multiple devices has multiple practical product applications. A plurality of the devices may be configured for use in applications requiring complex articulation, and support construction, manufacturing, medical and domestic needs. In particular, multiple devices may be configured to operate much like artificial fingers 112 (FIG. 39) for uses as mundane as animal waste removal, to the interconnection of building materials (FIG. 35), to sophisticated assembly line production, and microswitch actuators.

In medical applications, deploying multiple devices 10 permits multi-digit functionality, such as use of opposing devices (e.g. positioning two fingers 112 in opposition), or use of opposing ends of the same device 10 to function as forceps; scissors; and retraction devices attached to surfaces such as those shown in U.S. Pat. No. 6,309,349, and as seen in the literature such as that by ESTECH, of Danville, Calif.

Figure 40:
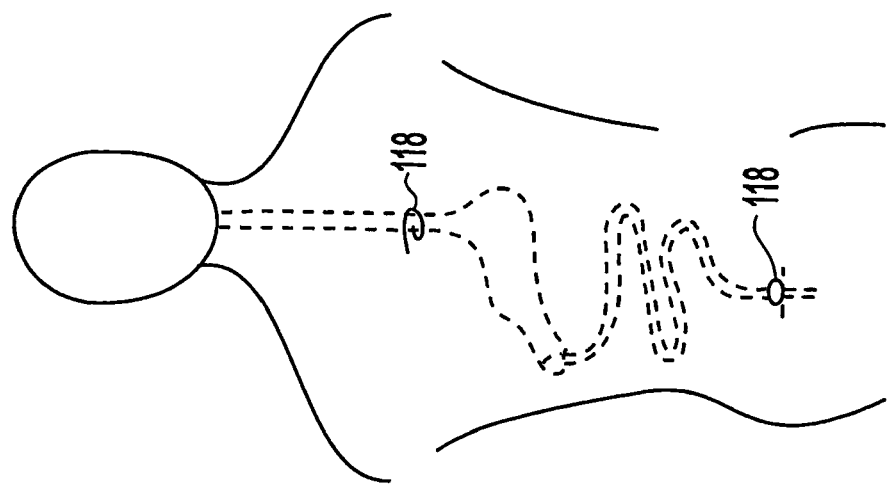
FIG. 40 is a schematic view of the fastener of the present invention in a representative application as a valve assist clamp for representative systems of a human.

Additional medical applications of interest include use of the device 10 of the present invention as an implantable temporary or permanent support 118 for weakened muscles or valves, as illustratively shown in FIG. 40, by way of example and not limitation, to support the gastric esophageal sphincter; or to assist relevant tissues and organs to prevent incontinence; or providing a plurality of devices 10 to assist peristaltic motion; or providing a valve for colostomy patients. In these applications, a pre-formed curvature from memory materials may be of value, as well as tensioning members having elastic or elastomeric qualities to permit relative movement as needed for proper functioning. As well, the device 10 can be provided with a mechanical or electrical actuator to change the position of the tensioning member and expand or contract the device, as the case may require.

Further medical applications of interest include using the device of the present invention to assist in inserting and operating expandable devices needed by surgeons during surgery to block or hold organs and other tissues away from areas in which they are working. See FIG. 34. In addition to the configuration of snare 102 as shown, the snare could alternately circle the heart as illustrated in FIG. 34, but rather than continue around the heart, instead wrap helically around the proximal end of the device 10, forming a snare much like a slip knot. This alternate configuration, however, is not preferred.

As is apparent from the foregoing detailed description, methods for use of the device 10 are also disclosed. The methods comprises the placement of the device in a position for fastening, whether by physical location or insertion into a material, deformation of the device 10, and manipulation of the device 10 in accordance with the steps that are presented in the process detailed in FIGS. 1-16 above.

A further aspect of the present invention is that the device may serve as a novelty device. In this regard, the articulated outer compression member may be operated with the tension member to provide an amusing toy for children, as well as for pets, particularly when combined with external ornamentation and other surface treatments of the device. The inner tensioning member may be provided with a means to temporarily secure the novelty device in a desired position. The device may also be mounted at the end of another device or stick with the tensioning member operable by the user, to provide amusement to a pet, such as a cat. Further, the device of the present invention may be provided as part of a set of building materials for play, including interconnecting features on the sides of the outer compression members, such as loops, clips, male/female or other connectors to interconnect with other devices 10, or with other components provided in a play set.

In yet a further aspect of the present invention, the device 10 may further be used in sports applications, including use at the end of a stick as a snare for animals, with the tensioning member operable by the user at the other end of the stick. Further, the device may be combined with a net and handle to produce a closeable net to capture butterflies, fish, small animals or other targets. In this regard, the handle could be could be attached to the device, where the inner tensioning member is operable by the user holding the handle, with a net attached to the handle. The net would be positioned with an opening, and the articulated device laced through the net so that application of tension to the outer compression member will substantially close the net. Curvature of the device and force multiplication combine to rapidly close the net.

Finally, in accordance with the present invention, the device 10 may be further applied in the garment industry to provide clothing adjustment features through a loop which permits multiple size adjustments with a minimum of fastener elements. A single fastener and loop may be used for a wide range of adjustment. In addition, the clothing adjustment may also provide body shaping functionality, such as is possible in positioning the device 10 as a support element in female garments, such as an underwire in a brassiere to provide comfort and shaping for the wearer.

The invention has been described with reference to the preferred embodiments. Obviously, modifications and alterations will occur to others upon reading and understanding the proceeding detailed description. As illustrated herein, applications may be at the scale of a known fastening devices down to sizes useful with microscale and nanoscale devices. It is intended that the invention be construed as including all such modifications and alterations insofar as they come within the scope of the appended claims or the equivalents thereof.

What is claimed is:

1. A fastener device comprising:
   an articulated compression member capable of being reconfigured by compression from a first configuration to a second configuration;
   at least one frangible container that ruptures upon reconfiguration of the compression member; and
   a tensioning member operably connected with the compression member for selectively applying compressive force to the compression member;
   wherein the compression member comprises a plurality of interconnected sections, each section having a mating feature protruding from one surface of the section and a plurality of detents on an opposing surface of the section, the mating feature interacting with one of the detents to lock adjacent sections in a desired relationship.

2. The fastener device of claim 1, further including a displacement detection device positioned to detect a change in configuration of at least a portion of the compression element.

3. The fastener device of claim 1, wherein the compression member further includes a functional surface element, at least a portion of which is positioned to contact a target when the compression member is in the second configuration.

4. The fastener device of claim 3 wherein the functional surface element includes one element from the group comprising: a cutting element, a heating element, a heat sealing element or combinations thereof.

5. The fastener device of claim 3 wherein the functional surface element includes at least one from the group of: adhesives, tackifiers and combinations thereof.

6. The fastener device of claim 1 wherein the compression member is selectively adjustable to deform into a plurality of shapes.

7. The fastener device of claim 1 wherein the compression member further includes a distal end and a proximal end, and wherein the end of the tensioning member for selectively applying compressive force is attached to the compression member at a point spaced from the distal and proximal ends.

8. The fastener device of claim 1 wherein the tensioning member comprises a temperature sensitive element that reconfigures and applies compression to the compression member in response to a change in temperature.

9. The fastener device of claim 1 wherein the tensioning member comprises a variable volume element that applies tension by varying the volume of said element.

10. The fastener device of claim 1, wherein the at least one frangible container includes a material from the group comprising: chemicals, stimuli sensitive polymers, nuclear materials, biologically active ingredients, antibiotics, anti-inflammatories, hormones, cells, DNA, medicaments, pharmaceutical active ingredients and combinations thereof.

11. The fastener device of claim 1 further comprising a piezo electric device attached to said tensioning member, said piezo electric device operable to increase or decrease the tension on the tensioning member.

12. The fastener device of claim 1 in said second configuration, wherein in said second configuration said fastener includes at least one loop of a generally helical shape.

13. The fastener device of claim 12 wherein the fastener is a medical device chosen from the group comprising: a snare, a stomach belt, a surgical clamp, an external aneurysm support, a muscle support, a valve or combinations thereof.

14. The fastener device of claim 12 wherein the medical device is a device chosen from the group comprising: a stent, an occlusive device, an expansion device, a stent, a muscle support, a valve or combinations thereof.

15. The fastener device of claim 1, wherein each section further comprises an inner channel, and the tensioning member runs through the inner channel of each section.

16. The fastener device of claim 15, wherein each section further comprises a guide on a side of each section and an inner channel; wherein the tensioning member runs through the guide of each section; and wherein the fastener further comprises an inner spine that runs through the inner channel of each section.

17. The fastener device of claim 1, wherein the mating feature is a protruding surface.

18. A method for fastening, comprising the steps of:
   providing a first portion of material to which a fastener is to be fastened;
   positioning at least a portion of a fastener in fastening relationship with the first portion of material, the fastener comprising:
     a compression member capable of reconfiguration from a first configuration to a second fastening configuration by compression;
     at least one frangible container that ruptures upon reconfiguration of the compression member; and
     a tensioning member operably connected with the compression member for selectively applying compressive force to the compression member;
     wherein the compression member comprises a plurality of interconnected sections, each section having a mating feature protruding from one surface of the section and a plurality of detents on an opposing surface of the section, the mating feature interacting with one of the detents to lock adjacent sections in a desired relationship;
   initiating reconfiguration of the fastener from the first position by applying tension to the tensioning member;
   compressing the compression member with the tensioning member and substantially reconfiguring the fastener to the second configuration wherein said fastener is in a fastening relationship with the first portion of material; and
   rupturing the at least one frangible container to release a substance upon compressing of the compression member.

19. The method of claim 18 wherein the step of substantially reconfiguring the fastener to the second configuration comprises reconfiguring the fastener into substantially one or more loops having a generally helical shape.

20. The method of claim 19 wherein said step of reconfiguring the fastener to a second configuration further includes establishing a fastening relationship surrounding a part of the first portion of material with the one or more loops.

21. The method of claim 20 wherein the first portion of material is a generally hollow structure, and wherein the step of establishing a fastening relationship with the first portion of material further comprises clamping said part of the first portion of material with the fastener to at least partially close the hollow structure.

22. The method of claim 20 wherein the fastener in its first position includes a medical device attached thereto, and wherein the step of establishing a fastening relationship further includes attaching a medical device to said first portion of material.

23. The method of claim 18 wherein the step of substantially reconfiguring the fastener to the second configuration comprises reconfiguring the fastener into a loop including a portion having a substantially helical shape, wherein the helical shape includes one or more loops.

24. The method of claim 18 wherein the first portion of material is a generally hollow structure, and the step of positioning at least a portion of a fastener in fastening relationship with a first portion of material comprises inserting the fastener in a generally linear first configuration inside the generally hollow structure, and the step of substantially reconfiguring the fastener to the second configuration comprises reconfiguring the fastener into substantially one or more loops having a generally helical shape, wherein at least a portion of the loops engage the inside surfaces of the generally hollow structure to fasten to the first portion of material.

25. The method of claim 24 wherein the step of reconfiguring the fastener to the second configuration and engaging the inside surfaces of the generally hollow structure further includes expanding the inside surface of the structure and opening an occlusion.

26. The method of claim 24 wherein the one or more loops in the second configuration of the fastener are variable between a first and second radius, the first radius is larger than the second radius, and the method further includes the step of reconfiguring the fastener between the first and second radii and at least partially occluding the generally hollow structure.

27. The method of claim 18 wherein said second configuration comprises a generally curved end, and said fastening relationship comprises extending said generally curved end into an opening in said first portion of material.

28. A method for fastening, comprising the steps of:
providing a first and second portion of material to be fastened;
positioning at least a portion of a fastener in fastening relationship with the first portion of material, the fastener comprising:
a compression member capable of reconfiguration from a first configuration to a second fastening configuration by compression;
at least one frangible container that ruptures upon reconfiguration of the compression member; and
a tensioning member operably connected with the compression member for selectively applying compressive force to the compression member;
wherein the compression member comprises a plurality of interconnected sections, each section having a mating feature protruding from one surface of the section and a plurality of detents on an opposing surface of the section, the mating feature interacting with one of the detents to lock adjacent sections in a desired relationship
initiating reconfiguration of the fastener from the first position by applying tension to the tensioning member;
positioning the fastener in fastening relationship with the second portion of material;
compressing the compression member with the tensioning member and substantially reconfiguring the fastener to the second configuration wherein said fastener is in a fastening relationship with both the first and second portions of material; and
rupturing the at least one frangible container to release a substance upon compressing of the compression member.

29. The method for fastening of claim 28, wherein in said first configuration the compression member is generally linear, and in said second configuration said compression member is generally curvilinear.

30. The method of claim 29, wherein the second configuration is one of a plurality of second configurations.

31. The method for fastening of claim 29, wherein the step of substantially reconfiguring the fastener to a second configuration comprises forming a plurality of loops.

32. The method for fastening of claim 31, wherein the plurality of loops define a helix.

33. The method for fastening of claim 28, further comprising the steps of: releasably securing the tensioning member after the step of substantially reconfiguring the fastener to the second configuration; and substantially maintaining the fastener in the second configuration.

* * * * *